(12) United States Patent
Kite et al.

(10) Patent No.: US 8,828,317 B2
(45) Date of Patent: *Sep. 9, 2014

(54) ANTISEPTIC COMPOSITIONS, METHODS AND SYSTEMS

(71) Applicant: Aseptica, Inc., Port Orchard, WA (US)

(72) Inventors: Peter Kite, West Yorkshire (GB); David Hatton, Port Orchard, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/147,443

(22) Filed: Jan. 3, 2014

(65) Prior Publication Data

US 2014/0194518 A1   Jul. 10, 2014

Related U.S. Application Data

(63) Continuation of application No. 13/942,634, filed on Jul. 15, 2013, now Pat. No. 8,703,053, which is a continuation of application No. 10/659,413, filed on Sep. 10, 2003, now Pat. No. 8,541,472, and a continuation-in-part of application No. 10/313,844, filed on Dec. 5, 2002, now abandoned.

(60) Provisional application No. 60/476,274, filed on Jun. 4, 2003, provisional application No. 60/338,639, filed on Dec. 5, 2001.

(51) Int. Cl.
*A61L 2/18* (2006.01)
*A61K 31/13* (2006.01)
*A01N 37/44* (2006.01)
*A01N 31/02* (2006.01)

(52) U.S. Cl.
CPC ............... *A01N 37/44* (2013.01); *A01N 31/02* (2013.01)
USPC ............................................. 422/28; 514/566

(58) Field of Classification Search
USPC ............................................. 422/28; 514/566
See application file for complete search history.

(56) References Cited

U.S. PATENT DOCUMENTS 6,267,979 B1 * 7/2001 Raad et al. .................... 424/405
2003/0153983 A1 * 8/2003 Miller et al. ................. 623/23.7

* cited by examiner

*Primary Examiner* — Sean E Conley

(57) ABSTRACT

Antiseptic compositions comprising at least one salt of EDTA are disclosed. These compositions have broad spectrum antimicrobial and antifungal activity and they also have anticoagulant properties. The antiseptic compositions have also demonstrated activity in penetrating and breaking down microbial slime, or biofilms. They are safe for human and medical uses and may be used as prophylactic preparations to prevent infection, or to reduce the proliferation of and/or eliminate existing or established infections.

14 Claims, 16 Drawing Sheets

FIGURE 1A

| Organism ID | Di-potassium EDTA | | Di-ammonium EDTA | | Di-sodium EDTA | | Tri-sodium EDTA | | Tetra-sodium EDTA | |
|---|---|---|---|---|---|---|---|---|---|---|
| | MIC | MBC | MIC | MBC | MIC | MBC | MIC | MBC | MIC | MBC |
| S24 Staph. epidermidis | <0.5 | 8 | <0.5 | 4 | <0.5 | <0.5 | <0.5 | <0.5 | <0.5 | <0.5 |
| 31 Staph. epidermidis | <0.5 | 8 | <0.5 | 8 | <0.5 | <0.5 | <0.5 | <0.5 | <0.5 | <0.5 |
| 301 Staph. xylosus | <0.5 | 6 | <0.5 | 4 | <0.5 | <0.5 | <0.5 | <0.5 | <0.5 | 20 |
| 300 Staph.capitis | <0.5 | 10 | <0.5 | 8 | <0.5 | <0.5 | <0.5 | <0.5 | <0.5 | 10 |
| J46 Staph.lentus | <0.5 | 10 | <0.5 | 10 | <0.5 | <0.5 | <0.5 | <0.5 | <0.5 | <0.5 |
| S24 Staph.capitis | <0.5 | 8 | <0.5 | 10 | <0.5 | <0.5 | <0.5 | <0.5 | <0.5 | <0.5 |
| R8 Staph. simulans | <0.5 | 8 | <0.5 | 10 | <0.5 | 1 | <0.5 | 1.5 | <0.5 | 1 |
| 72 S.aureus | 1 | 6 | 1 | 6 | <0.5 | <0.5 | <0.5 | <0.5 | <0.5 | <0.5 |
| R57 S.aureus | 1 | 8 | 1 | 10 | <0.5 | 10 | <0.5 | <0.5 | <0.5 | 8 |
| R13 S.aureus | 1 | 6 | 1 | 15 | <0.5 | 10 | <0.5 | <0.5 | <0.5 | <0.5 |
| R30 S.aureus | 1 | 8 | 1 | 15 | <0.5 | 10 | <0.5 | <0.5 | ----- | ----- |
| 8 S.aureus | 1 | 8 | 1 | 10 | <0.5 | <0.5 | <0.5 | <0.5 | ----- | ----- |
| R64 MRSA | 1 | 6 | 1 | 8 | <0.5 | <0.5 | <0.5 | <0.5 | <0.5 | <0.5 |

FIGURE 1B

| Organism ID | Di-potassium EDTA MIC | Di-potassium EDTA MBC | Di-ammonium EDTA MIC | Di-ammonium EDTA MBC | Di-sodium EDTA MIC | Di-sodium EDTA MBC | Tri-sodium EDTA MIC | Tri-sodium EDTA MBC | Tetra-sodium EDTA MIC | Tetra-sodium EDTA MBC |
|---|---|---|---|---|---|---|---|---|---|---|
| R51 MRSA | 1 | 10 | 1 | 6 | <0.5 | 1 | <0.5 | <0.5 | <0.5 | <0.5 |
| R92 MRSA | 1 | 8 | 1 | >15 | <0.5 | 10 | <0.5 | <0.5 | <0.5 | <0.5 |
| S93 MRSA | 1 | 8 | 1 | 10 | <0.5 | <0.5 | <0.5 | <0.5 | <0.5 | <0.5 |
| J67 MRSA | 1 | 8 | 1 | 10 | <0.5 | 10 | <0.5 | <0.5 | <0.5 | <0.5 |
| R8 VRE | <0.5 | 8 | <0.5 | 15 | <0.5 | 100 | <0.5 | 20 | <0.5 | 30 |
| Woods VRE | 1 | 8 | 1 | >15 | <0.5 | 100 | <0.5 | 2 | <0.5 | 1 |
| S77 Enterococcus Faecium | <0.5 | 8 | <0.5 | 15 | <0.5 | 100 | <0.5 | 20 | <0.5 | 6 |
| S76 Enterococcus faecalis | 1 | 15 | 1 | 15 | <0.5 | 100 | <0.5 | 1.5 | <0.5 | 40 |
| 68 Klebsiella pneumoniae | 1.5 | 15 | 4 | >10 | 8 | 60 | 20 | 40 | 6 | 6 |
| R51 Klebsiella pneumoniae | 1 | 15 | 1.5 | >10 | ----- | ----- | ----- | ----- | ----- | ----- |
| 128 Klebsiella oxytoca | 1 | 15 | 1 | >10 | 1 | 90 | 4 | 20 | 4 | 6 |
| J7 Klebsiella ornitholytica | 1 | >15 | 1 | >10 | 1 | 60 | 20 | 70 | 4 | 8 |
| 250 E. coli | 1 | >15 | 1 | >10 | 1.5 | 80 | 10 | 20 | 1.5 | 1.5 |
| B/C E. coli | 1 | 15 | 1.5 | >10 | ----- | ----- | ----- | ----- | ----- | ----- |

FIGURE 1C

| Organism ID | Di-potassium EDTA | | Di-ammonium EDTA | | Di-sodium EDTA | | Tri-sodium EDTA | | Tetra-sodium EDTA | |
|---|---|---|---|---|---|---|---|---|---|---|
| | MIC | MBC | MIC | MBC | MIC | MBC | MIC | MBC | MIC | MBC |
| 137 E. coli | 1 | 15 | 4 | >10 | 4 | 60 | 4 | 10 | 2 | 2 |
| 292 Ent. cloacae | 4 | 15 | 4 | >10 | 4 | >100 | 20 | 20 | 6 | 15 |
| 190 Ent. cloacae | 4 | >15 | 4 | >10 | 4 | 100 | 20 | 20 | 6 | 15 |
| J22 Ent. cloacae | 6 | >15 | <0.5 | >10 | 6 | >100 | 20 | 20 | 6 | 10 |
| R4 Steno. maltophilia | <0.5 | 10 | 1 | >10 | ----- | ----- | ----- | ----- | ----- | ----- |
| B/C Pseudomonas aeruginosa | 1 | >15 | 1 | >10 | ----- | ----- | ----- | ----- | ----- | ----- |
| J20 Pseudomonas aeruginosa | 1 | >15 | 1 | >10 | <0.5 | 50 | 4 | 20 | 2 | 4 |
| J26 Pseudomonas sp. | 1 | 15 | <0.5 | >10 | <0.5 | 25 | 4 | 60 | 8 | 4 |
| R75 Coryne. amycolatum | <0.5 | <0.5 | <0.5 | 1 | NG | NG | NG | NG | <0.5 | 20 |
| R23 Coryne. strait/amy | <0.5 | <0.5 | <0.5 | 1 | NG | NG | NG | NG | <0.5 | <0.5 |
| 177 Acinetobacter baumanii | <0.5 | <0.5 | <0.5 | <0.5 | <0.5 | <0.5 | <0.5 | <0.5 | <0.5 | <0.5 |
| J44 Acinetobacter baumanii | <0.5 | 60-70 | <0.5 | >10 | <0.5 | 1 | <0.5 | <0.5 | <0.5 | <0.5 |

FIGURE 1D

| Organism ID | Di-potassium EDTA | | Di-ammonium EDTA | | Di-sodium EDTA | | Tri-sodium EDTA | | Tetra-sodium EDTA | |
|---|---|---|---|---|---|---|---|---|---|---|
| | MIC | MBC | MIC | MBC | MIC | MBC | MIC | MBC | MIC | MBC |
| R16 Proteus mirabilis | <0.5 | >15 | <0.5 | >10 | <0.5 | 50 | <0.5 | 40 | <0.5 | 15 |
| R81 Proteus vulgaris | 1 | >15 | <0.5 | >10 | <0.5 | 15 | <0.5 | 40 | <0.5 | 8 |
| R26 Proteus mirabilis | <0.5 | 15 | <0.5 | >10 | <0.5 | 50 | <0.5 | 60 | 1 | 15 |

FIGURE 2

| Organism ID | Tetra-sodium MIC | Tetra-sodium MBC | Di-potassium MIC | Di-potassium MBC | Di-ammonium MIC | Di-ammonium MBC |
|---|---|---|---|---|---|---|
| J96 Candida albicans | 0.5 | 15 | 0.5 | >100 | 0.5 | >100 |
| J92 Candida albicans | 0.5 | 15 | 0.5 | >100 | 0.5 | >100 |
| Myc. Candida albicans | 0.5 | 0.5 | 0.5 | >100 | 0.5 | >100 |
| I98 Candida lucitaniae | 0.5 | 6 | 0.5 | >100 | 0.5 | >100 |
| Myc. Candida tropicalis | 0.5 | 10 | 1 | >100 | 1 | 100 |
| Myc. Candida Guilliermondii | 0.5 | 0.5 | 0.5 | >100 | 0.5 | >100 |
| Myc. Candida glabrata | 0.5 | 2 | 0.5 | >100 | 0.5 | 90 |
| Myc. Candida parapsilosis | 0.5 | 8 | 0.5 | >100 | 0.5 | 100 |
| J96 Candida glabrata | 0.5 | 8 | 0 | 100 | 0.5 | >100 |

FIGURE 3A

| Organism ID | Cupric Di-sodium EDTA | | Magnesium Di-sodium EDTA | | Ferric sodium EDTA | |
|---|---|---|---|---|---|---|
| | MIC | MBC | MIC | MBC | MIC | MBC |
| S24 Staph. epidermidis | <0.5 | <0.5 | 6 | 30 | >20 | >30 |
| 31 Staph. epidermidis | <0.5 | <0.5 | 6 | 30 | >20 | >30 |
| 301 Staph. xylosus | <0.5 | <0.5 | 2 | >30 | >20 | >30 |
| 300 Staph. capitis | <0.5 | <0.5 | 1.5 | >30 | >20 | >30 |
| J46 Staph. lentus | <0.5 | <0.5 | 6 | >30 | >20 | >30 |
| S24 Staph. capitis | <0.5 | <0.5 | 6 | >30 | >20 | >30 |
| R8 Staph. simulans | <0.5 | <0.5 | 1.5 | >30 | >20 | >30 |
| 72 S.aureus | <0.5 | <0.5 | >30 | >30 | >20 | >30 |
| R57 S.aureus | <0.5 | <0.5 | >30 | >30 | >20 | >30 |
| R13 S.aureus | <0.5 | <0.5 | >30 | >30 | >20 | >30 |
| R30 S.aureus | <0.5 | <0.5 | >30 | >30 | >20 | >30 |
| 8 S.aureus | <0.5 | <0.5 | >30 | >30 | >20 | >30 |
| R64 MRSA | <0.5 | <0.5 | >30 | >30 | >20 | >30 |
| R51 MRSA | <0.5 | <0.5 | >30 | >30 | >20 | >30 |
| R92 MRSA | <0.5 | <0.5 | >30 | >30 | >20 | >30 |
| S93 MRSA | <0.5 | <0.5 | 25 | >30 | >20 | >30 |
| J67 MRSA | <0.5 | <0.5 | >30 | >30 | 2 | >30 |
| R8 VRE | >30 | >30 | >30 | >30 | >20 | >30 |
| Woods VRE | <0.5 | <0.5 | 1.5 | >30 | 4 | >30 |
| S77 Entero-coccus faecium | <0.5 | <0.5 | >30 | >30 | 4 | >30 |
| S76 Entero-coccus faecalis | >30 | >30 | >30 | >30 | >15 | >15 |
| 68 Klebsiella pneumoniae | >30 | >30 | >30 | >30 | 15 | >15 |
| R51 Klebsiella pneumoniae | | | | | | |

FIGURE 3B

| Organism ID | Cupric Di-sodium EDTA | | Magnesium Di-sodium EDTA | | Ferric sodium EDTA | |
|---|---|---|---|---|---|---|
| | MIC | MBC | MIC | MBC | MIC | MBC |
| 128 Klebsiella oxytoca | >30 | >30 | >30 | >30 | >15 | >15 |
| J7 Klebsiella ornitholytica | >30 | >30 | >30 | >30 | 15 | >15 |
| 250 E. coli | >30 | >30 | >30 | >30 | 15 | >15 |
| B/C E. coli | 6 | >30 | >30 | >30 | >15 | >15 |
| 137 E. coli | >30 | >30 | >30 | >30 | >15 | >15 |
| 292 Ent. cloacae | >30 | >30 | >30 | >30 | >15 | >15 |
| 190 Ent. cloacae | >30 | >30 | >30 | >30 | >15 | >15 |
| J22 Ent. cloacae | 6 | 8 | >30 | >30 | >15 | >15 |
| R4 Steno. maltophilia | 6 | >30 | >30 | >30 | 10 | 10 |
| B/C Pseudomonas aeruginosa | >30 | >30 | >30 | >30 | 15 | >15 |
| J20 Pseudomonas aeruginosa | >30 | >30 | >30 | >30 | 15 | >15 |
| J26 Pseudomonas sp. | >30 | >30 | >30 | >30 | 15 | >15 |
| R75 Coryne. amycolatum | <0.5 | <0.5 | <0.5 | 4 | 10 | 10 |
| R23 Coryne. strait/amy | <0.5 | <0.5 | <0.5 | 4 | 10 | 10 |
| 177 Acinetobacter baumanii | <0.5 | <0.5 | <0.5 | <0.5 | 6 | 10 |
| J44 Acinetobacter baumanii | 6 | 15 | >30 | >30 | >15 | >15 |
| R16 Proteus mirabilis | 6 | >30 | >30 | >30 | >15 | >15 |
| R81 Proteus vulgaris | >30 | >30 | >30 | .30 | >15 | >15 |
| R26 Proteus mirabilis | 6 | >30 | >30 | >30 | >15 | >15 |

FIGURE 4A

| Organism ID | Cupric Di-sodium+ tetrasodium EDTA | | Cupric Di-sodium + Di-potassium EDTA | | Cupric Di-sodium + Di-ammonium EDTA | |
|---|---|---|---|---|---|---|
| | MIC | MBC | MIC | MBC | MIC | MBC |
| S24 Staph. epidermidis | 0.25 | 2 | 0.25 | 15 | 0.5 | 20 |
| 31 Staph. epidermidis | 0.25 | 8 | 0.25 | 20 | 0.5 | 20 |
| 301 Staph. xylosus | <0.1 | >20 | <0.1 | >20 | <0.1 | 20 |
| 300 Staph. capitis | <0.1 | >20 | <0.1 | 20 | <0.1 | 20 |
| J46 Staph. lentus | 0.25 | 6 | 0.25 | 15 | 0.5 | 20 |
| S24 Staph. capitis | 0.25 | 8 | 0.25 | 20 | 0.5 | 20 |
| R8 Staph. simulans | 0.25 | >20 | 1 | >20 | 1 | 20 |
| 72 S.aureus | <0.1 | >20 | <0.1 | >20 | <0.1 | 20 |
| R57 S.aureus | <0.1 | >20 | <0.1 | 20 | <0.1 | 20 |
| R13 S.aureus | <0.1 | >20 | <0.1 | 20 | <0.1 | >20 |
| R30 S.aureus | <0.1 | 15 | <0.1 | 20 | <0.1 | >20 |
| 8 S.aureus | <0.1 | >20 | <0.1 | >20 | <0.1 | 20 |
| R64 MRSA | <0.1 | >20 | <0.1 | >20 | <0.1 | >20 |
| R51 MRSA | <0.1 | >20 | <0.1 | 20 | <0.1 | >20 |

FIGURE 4B

| Organism ID | Cupric Di-sodium + tetrasodium EDTA | | Cupric Di-sodium + Di-potassium EDTA | | Cupric Di-sodium + Di-ammonium EDTA | |
|---|---|---|---|---|---|---|
| | MIC | MBC | MIC | MBC | MIC | MBC |
| R92 MRSA | <0.1 | >20 | <0.1 | >20 | <0.1 | >20 |
| S93 MRSA | <0.1 | 15 | <0.1 | 20 | <0.1 | 20 |
| J67 MRSA | <0.1 | >20 | <0.1 | 20 | <0.1 | 20 |
| R8 VRE | 0.25 | 20 | 0.25 | 20 | 0.5 | >20 |
| Woods VRE | 0.25 | >20 | <0.1 | 20 | <0.1 | >20 |
| S77 Entero-coccus faecium | 0.5 | >20 | 0.5 | >20 | 1 | >20 |
| S76 Entero-coccus faecalis | 0.25 | >20 | <0.1 | >20 | <0.1 | >20 |
| 68 Klebsiella pneumoniae | 10 | >20 | 6 | >20 | 2 | >20 |
| R51 Klebsiella pneumoniae | 4 | >20 | 4 | >20 | 2 | >20 |
| 128 Klebsiella oxytoca | 4 | >20 | 2 | >20 | 2 | >20 |
| J7 Klebsiella ornitholytica | 6 | >20 | 2 | >20 | 2 | >20 |
| 250 E. coli | 6 | 15 | 2 | >20 | 2 | >20 |
| B/C E. coli | 6 | 1 | 2 | >20 | 2 | >20 |
| 137 E. coli | 6 | 4 | 2 | >20 | 2 | >20 |
| 292 Ent. cloacae | 20 | >20 | 8 | >20 | 8 | >20 |

FIGURE 4C

| Organism ID | Cupric Di-sodium + tetrasodium EDTA | | Cupric Di-sodium + Di-potassium EDTA | | Cupric Di-sodium + Di-ammonium EDTA | |
| --- | --- | --- | --- | --- | --- | --- |
| | MIC | MBC | MIC | MBC | MIC | MBC |
| 190 Ent. cloacae | 20 | >20 | 8 | >20 | 6 | >20 |
| J22 Ent. cloacae | 20 | >20 | 8 | >20 | 6 | >20 |
| R4 Steno. maltophilia | 6 | 10 | 1 | >20 | 1 | >20 |
| B/C Pseudo-monas aeruginosa | 6 | 10 | 2 | >20 | 2 | >20 |
| J20 Pseudo-monas aeruginosa | 6 | 15 | 2 | >20 | 2 | >20 |
| J26 Pseudo-monas sp. | 6 | >20 | 2 | >20 | 2 | >20 |
| R75 Coryne. amycolatum | <0.1 | <0.1 | 0.25 | 0.25 | 0.25 | 0.25 |
| R23 Coryne. strait/amy | 6 | 10 | 1 | >20 | 1 | >20 |
| 177 Acineto-bacter baumanii | 6 | 0.5 | 0.5 | 0.25 | 0.25 | <0.1 |
| J44 A. baumanii | 6 | >20 | 2 | >20 | 1 | >20 |
| R16 Proteus mirabilis | 6 | >20 | 2 | >20 | 1 | >20 |
| R81 Proteus vulgaris | 6 | >20 | 2 | >20 | 2 | >20 |
| R26 Proteus mirabilis | 6 | >20 | 2 | >20 | 1 | >20 |

FIGURE 5A

| Organism ID | Tetrasodium + Di-ammonium EDTA | | Tetrasodium + Di-potassium EDTA | | Di-ammonium + Di-potassium EDTA | |
|---|---|---|---|---|---|---|
| | MIC | MBC | MIC | MBC | MIC | MBC |
| S24 Staph. epidermidis | 0.5 | >20 | 1 | 20 | 0.5 | >8 |
| 31 Staph. epidermidis | 0.5 | >20 | 1 | 6 | 0.5 | >8 |
| 301 Staph. xylosus | 0.5 | >20 | 1 | >20 | 0.5 | >8 |
| 300 Staph. capitis | 0.5 | >20 | 0.5 | >20 | 0.5 | 8 |
| J46 Staph. lentus | 0.5 | >20 | 0.5 | 8 | 0.5 | >8 |
| S24 Staph. capitis | 0.5 | >20 | 0.5 | 8 | 0.5 | >8 |
| R8 Staph. simulans | 0.5 | >20 | 0.5 | >20 | 0.5 | >8 |
| 72 S.aureus | 1 | >20 | 1 | 20 | 0.5 | 8 |
| R57 S.aureus | 1 | >20 | 1 | 20 | 1 | >8 |
| R13 S.aureus | 0 | 0 | 0 | 0 | 0 | 0 |
| R30 S.aureus | 1 | 4 | 1 | 4 | 1 | 8 |
| 8 S.aureus | 1 | >20 | 1 | 20 | 1 | 8 |
| R64 MRSA | 1 | >20 | 1 | 20 | 1 | >8 |
| R51 MRSA | 1 | >20 | 1 | 20 | 0.5 | >8 |

FIGURE 5B

| Organism ID | Tetrasodium + Di-ammonium EDTA | | Tetrasodium + Di-potassium EDTA | | Di-ammonium + Di-potassium EDTA | |
|---|---|---|---|---|---|---|
| | MIC | MBC | MIC | MBC | MIC | MBC |
| R92 MRSA | 1 | >20 | 1 | >20 | 1 | >8 |
| S93 MRSA | 1 | >20 | 1 | 20 | 1 | 8 |
| J67 MRSA | 1 | >20 | 1 | >20 | 1 | 8 |
| R8 VRE | 1 | >20 | 1 | >20 | 1 | >8 |
| Woods VRE | 1 | >20 | 1 | >20 | 1 | >8 |
| S77 Entero-coccus faecium | 0.5 | >20 | 1 | >20 | 1 | >8 |
| S76 Entero-coccus faecalis | 1 | >20 | 1 | >20 | 1 | >8 |
| 68 Klebsiella pneumoniae | >20 | >20 | >20 | >20 | 10 | >10 |
| R51 Klebsiella pneumoniae | 1 | >20 | 1 | >20 | 1 | >10 |
| 128 Klebsiella oxytoca | 1 | >20 | 1 | >20 | 1 | >10 |
| J7 Klebsiella ornitholytica | >20 | >20 | 20 | >20 | 10 | >10 |
| 250 E. coli | >20 | >20 | 20 | >20 | 2 | >10 |
| B/C E. coli | 1 | 0.5 | 1 | 1 | 0.5 | >10 |
| 137 E. coli | 4 | >20 | 20 | >20 | 1 | >10 |
| 292 Ent. cloacae | 8 | >20 | >20 | >20 | 4 | >10 |

FIGURE 5C

| Organism ID | Tetrasodium + Di-ammonium EDTA | | Tetrasodium + Di-potassium EDTA | | Di-ammonium + Di-potassium EDTA | |
|---|---|---|---|---|---|---|
| | MIC | MBC | MIC | MBC | MIC | MBC |
| 190 Ent. cloacae | >20 | >20 | >20 | >20 | 6 | >10 |
| J22 Ent. cloacae | >20 | >20 | >20 | >20 | 4 | >10 |
| R4 Steno. maltophilia | 1 | >20 | 1 | >20 | 0.5 | >10 |
| B/C Pseudo-monas aeruginosa | 8 | >20 | 15 | 15 | 2 | >10 |
| J20 Pseudo-monas aeruginosa | 6 | >20 | 15 | 20 | 2 | >10 |
| J26 Pseudo-monas sp. | 8 | >20 | 20 | >20 | 2 | >10 |
| R75 Coryne. amycolatum | 0.5 | 4 | 0.5 | 1 | 0.5 | 2 |
| R23 Coryne. strait/amy | 0.5 | 0.5 | 0.5 | 0.5 | 0.5 | 0.5 |
| 177 Acinetobacter baumanii | 4 | 8 | 1 | >20 | 0.5 | >10 |
| J44 A. baumanii | >20 | >20 | >20 | >20 | 2 | >10 |
| R16 Proteus mirabilis | 1 | >20 | 1 | >20 | 0.5 | >10 |
| R81 Proteus vulgaris | 1 | >20 | 1 | >20 | 0.5 | >10 |
| R26 Proteus mirabilis | >20 | >20 | >20 | >20 | 2 | >10 |

FIGURE 6

| Organism | Tetra-sodium EDTA MBEC (mg/ml, w/v) |
|---|---|
| 31 Staph. epidermidis | 20-40 |
| 301 Staph. xylosus | 20-40 |
| 300 Staph. capitis | <5 |
| J46 Staph. lentus | <5 |
| R8 Staph. simulans | 20-40 |
| 72 Staph. aureus | <5 |
| R57 Staph. aureus | <5 |
| 8 Staph. aureus | <5 |
| R92 MRSA | <5 |
| S93 MRSA | <5 |
| J67 MRSA | <5 |
| 68 Klebsiella pneumoniae | <5 |
| J7 Klebsiella ornitholytica | <5 |
| 292 Enterobacter cloacae | <5 |
| 190 Enterobacter cloacae | 20 |
| J22 Enterobacter cloacae | 15 |
| R4 Stenotrophomonas maltophilia | <20 |
| J20 Pseudomonas aeruginosa | <10 |
| J26 Pseudomonas aeruginosa | <5 |
| J44 Acinetobacter baumanii | 10 |
| R16 Proteus mirabilis | <5 |
| R81 Proteus vulgaris | <5 |
| H Enterococcus | <5 |
| 7097651 E. coli | <5 |
| 250 E. coli | <10 |
| 7115649 Klebsiella oxytoca | <5 |

FIGURE 7

| Catheter ID | EDTA Conc. (mg/mL) | Colony count at 0 hours (cfu/mL) | Colony count at 3 hours (cfu/mL) | Colony count at 6 hours (cfu/mL) | Colony count at 24 hours (cfu/mL) | Organisms Present |
|---|---|---|---|---|---|---|
| G | 40 | >100000 | 120000 | 6000 | 0 | Mixed Gram-ve and Gram+ve cultures |
| H | 40 | >100000 | 80000 | 0 | 0 | Mixed Gram-ve and Gram+ve cultures |
| I | 40 | 200000 | >500000 | 25000 | 0 | CNS + Coryneforms |
| J | 40 | >500000 | 180000 | 0 | 0 | CNS |
| K | 40 | >1000000 | 600000 | 500000 | 180000 | Streptococcus sp., CNS and Gram-ve bacillus |
| P | 40 | >500000 | 2500000 | 150000 | 54500 | Pseudomonas sp. + Streptococcus sp. |
| Q | 40 | 205000 | 650000 | 1000 | 5500 | Enterococcus sp. |
| R | 40 | 5000 | 500 | 0 | 0 | MRSA |
| S | 40 | >500000 | 100000 | 30000 | 0 | CNS |
| T | 40 | 137500 | 1000 | 0 | 0 | MRSA |
| U | 40 | >500000 | 182500 | 67500 | 13500 | CNS |
| V | 40 | 700000 | 38500 | 37500 | 13000 | CNS + Group D Streptococcus |
| W | 40 | >500000 | 0 | 0 | 0 | Enterobacter cloacae |
| X | 40 | >500000 | 20000 | 0 | 0 | Mixed CNS |
| Z | 40 | >500000 | 0 | 0 | 0 | CNS |
| A1 | 40 | 700000 | 37000 | 60000 | 0 | MRSA |
| B1 | 40 | 24000 | 0 | 0 | 0 | MRSA |

FIGURE 8

| Catheter ID | EDTA Conc. (mg/mL) | Colony count at 0 hours (cfu/mL) | Colony count at 3 hours (cfu/mL) | Colony count at 6 hours (cfu/mL) | Colony count at 24 hours (cfu/mL) | Organisms Present |
|---|---|---|---|---|---|---|
| A | 100 | 10000000 | 0 | 0 | 0 | CNS |
| B | 100 | 10000000 | 100 | 200 | 0 | CNS |
| C | 50 | 10000000 | 0 | 0 | 0 | Mixed coliforms |
| D | 20 | >100000 | 250000 | 100000 | 0 | Mixed Gram-ve and Gram+ve cultures |
| E | 30 | >100000 | 400000 | 360000 | 0 | Mixed Gram-ve and Gram+ve cultures |
| F | 30 | 300000 | 57000 | 2000 | 0 | Mixed Gram-ve and Gram+ve cultures |
| L | 60 | 600000 | 5000 | 4000 | 0 | Enterococcus sp. |
| M | 60 | >500000 | 300000 | 17000 | 17000 | Proteus sp. and CNS |
| O | 50 | 500000 | 30000 | 130000 | 0 | Staphylococcus aureus |
| N (arterial) | 50 | 500000 | 10000 | 0 | 0 | CNS |
| N (venous) | 50 | 300000 | 10000 (CNS only) | 60000 (CNS only) | 0 | Klebsiella pneumoniae + CNS |

ANTISEPTIC COMPOSITIONS, METHODS AND SYSTEMS

PRIORITY CLAIM TO PRIOR APPLICATIONS

This application is a continuation of U.S. patent application Ser. No. 10/659,413, entitled "Antiseptic Compositions, Methods and Systems," filed Sep. 9, 2003, which claims priority to U.S. Provisional Patent Application No. 60/476,274 filed Jun. 4, 2003. U.S. patent application Ser. No. 10/659,413 is also a continuation-in-part of U.S. patent application Ser. No. 10/313,844, filed Dec. 5, 2002, which claims priority to U.S. Provisional Patent Application No. 60/338,369 filed Dec. 5, 2001.

TECHNICAL FIELD OF THE INVENTION

The present invention relates to antiseptic compositions, methods and systems for use in various medical applications, as well as sanitizing applications in general, including industrial and environmental sanitizing applications. Compositions of the present invention have antimicrobial, anti-fungal, anti-viral and anti-amoebic properties and may also serve as anti-coagulants. Specified salts and compositions of ethylene diamine tetraacetic acid (EDTA) ($C_{10}H_{12}N_2Na_4O_8$) are used at specified concentrations and pH levels. Exemplary applications include inhibiting, reducing or eliminating the presence of microbial and/or fungal organisms on surfaces, or in solutions, or in a complexed form, such as in biofilms. Exemplary applications and methods include providing an antiseptic coating on surfaces of objects to reduce the incidence of infection, and contacting objects and/or surfaces by flushing, soaking and/or rinsing with an antiseptic solution to inhibit the proliferation of or to reduce or eliminate microbial populations.

BACKGROUND OF THE INVENTION AND DESCRIPTION OF PRIOR ART

Infections are a significant problem in many fields where sanitary conditions are important, such as in healthcare. Problematic infections may arise from bacterial, fungal, amoebic, protozoan and/or viral organisms. Challenges are encountered both in preventing infection, and in reducing or eliminating the infection once it is established. Infected environments may include surfaces of objects, fluids and fluid conduits and/or humans or animals.

Alcohol solutions and isopropyl alcohol wipes are commonly used to sanitize surfaces and have been shown to have antibacterial activity. The most effective inhibitory anti-microbial effect is seen with 70% isopropanol solutions. Alcohol solutions at this concentration are quite expensive and rapidly evaporate, which substantially diminishes their efficacy and increases their cost. Moreover, although isopropanol solutions may be used for surfaces, including human skin, and in a variety of medical applications, alcohol solutions of this concentration cannot be administered to humans, for medical purposes, other than topically.

In the healthcare field, infections of various types and causes are common and often result in longer hospital stays, producing higher hospital costs. Even worse, over 90,000 patient deaths annually are attributed to nosocomial infections—that is, infections acquired at a hospital or in another healthcare environment. Surveillance for nosocomial infection has become an integral part of hospital practice. Studies conducted more than 20 years ago by the Centers for Disease Control and Prevention (CDC) documented the efficacy of these surveillance activities in reducing nosocomial infection occurrence. Despite the attention paid to problems of nosocomial infection, however, infection rates have not been dramatically reduced, and nosocomial infections remain a substantial risk and a substantial health concern.

One problematic source of infections in the medical and veterinary fields is found in catheters, and particularly in in-dwelling catheters. Catheters have become essential in the management of critical care patients, yet the inside of a catheter is often the major source of infection. Catheters are used for delivery of fluids, blood products, drugs, nutrients, hemodialysis, hemofiltration, peritoneal dialysis, retrieval of blood samples, monitoring of patient conditions, etc. Transcutaneous catheters often become infected through skin penetration of the catheter. It has been found that seventy percent (70%) of all nosocomial bloodstream infections occur in patients with central venous catheters. Daouicher et al. 340, 1-8, NEW ENGLAND JOURNAL OF MEDICINE (1999).

In particular, during some procedures, a catheter must be implanted in, and remain implanted in, a patient for a relatively long period of time, e.g. over thirty days. Intravenous (IV) therapy catheters and urinary catheters typically remain implanted for a substantial period of time. As a result of trauma to the areas of insertion, and pain to the patients, such catheters can't be removed and implanted frequently. Catheter-borne bacteria are implicated as a primary source of urinary tract infections. Patients who receive a peripherally inserted central catheter during pregnancy have also been found to be at significant risk for infectious complications. "Complications Associated With Peripherally Inserted Central Catheter Use During Pregnancy" AM. J. OBSTET. GYNECOL. 188(5):1223-5 May 2003. In addition, central venous catheter infection, resulting in catheter related sepsis, has been cited as the most frequent complication during home parenteral nutrition. CLINICAL NUTRITION, 21(1):33-38, 2002. Because of the risk of infections, catheterization may be limited to incidences when the procedure is absolutely necessary. This seriously compromises patient health.

After most prescribed access medical procedures involving a catheter, the catheter is flushed with saline and then filled with a liquid, such as saline or a heparin solution, to prevent blood from clotting inside of the catheter, to inhibit the patient's blood from backing up into the catheter, and to prevent gases from entering the catheter. The liquid that is used to flush the catheter is referred to as a "lock-flush," and the liquid used to fill the catheter following flushing or during periods of non-use is referred to as a "lock" solution.

Traditionally, catheters have been locked with normal saline or heparin solutions, which provide anticoagulant activity. Heparin and saline are sometimes used in combination. Normal saline is generally used to lock short term peripheral intravenous catheters, but saline has no anticoagulant or antimicrobial activity. Heparin solutions are generally used to lock vascular catheters. Heparin has anticoagulant activity but it does not function as an antimicrobial and does not prevent or ameliorate infections. There are also strong indications that heparin in lock solutions may contribute to heparin-induced thrombocytopenia, a serious bleeding complication that occurs in a subset of patients receiving heparin injections.

Catheter locking solutions comprising Taurolidine, citric acid and sodium citrate have been proposed. A recent publication (Kidney International, September 2002) describes the use of a 70% alcohol solution as a lock solution for a subcutaneous catheter port. The use of alcohol as a lock solution is questionable, since it is not an anticoagulant, and since there would be risks associated with this solution entering the bloodstream. There is also no evidence that the inventors are aware of that indicates that a 70% alcohol solution has any biofilm eradication activity.

An emerging trend and recommendation from the Center for Infectious Disease (CID) is to treat existing catheter infections systemically with either a specific or a broad range antibiotic. Use of an antibiotic in a lock solution to prevent infection is not recommended. The use of antibiotics to treat existing catheter infections has certain risks, including: (1) the risk of antibiotic-resistant strains developing; (2) the inability of the antibiotic to kill sessile, to or deep-layer biofilm bacteria, which may require the use of antibiotics at toxic concentrations; and (3) the high cost of prolonged antibiotic therapy. Catheters coated with an antiseptic or antibiotic material are available. These coated catheters may only provide limited protection for a relatively short period of time.

In general, free-floating organisms may be vulnerable to antibiotics. However, bacteria and fungi may become impervious to antibiotics by attaching to surfaces and producing a slimy protective substance, often referred to as extra-cellular polymeric substance (EPS). As the microbes proliferate, more than 50 genetic up or down regulations may occur, resulting in the formation of a more antibiotic resistant microbial biofilm. One article attributes two-thirds of the bacterial infections that physicians encounter to biofilms. SCIENCE NEWS, 1-5 Jul. 14, 2001.

Biofilm formation is a genetically controlled process in the life cycle of bacteria that produces numerous changes in the cellular physiology of the organism, often including increased antibiotic resistance (of up to 100 to 1000 times), as compared to growth under planktonic (free floating) conditions. As the organisms grow, problems with overcrowding and diminishing nutrition trigger shedding of the organisms to seek new locations and resources. The newly shed organisms quickly revert back to their original free-floating phase and are once again vulnerable to antibiotics. However, the free-floating organism may enter the bloodstream of the patient, creating bloodstream infections, which produce clinical signs, e.g. fever, and more serious infection-related symptoms. Sessile rafts of biofilm may slough off and may attach to tissue surfaces, such heart valves, causing proliferation of biofilm and serious problems, such as endocarditis.

In industrial settings, the formation of biofilms is very common and is generally referred to as biofouling. For example, biofilm growth on mechanical structures, such as filtration devices, is a primary cause of biological contamination of drinking water distribution systems. Biofilm formation in industrial settings may lead to material degradation, product contamination, mechanical blockage and impedance of heat transfer in processing systems. Biofilm formation and the resultant contamination is also a common problem in food preparation and processing facilities.

To further complicate matters, conventional sensitivity tests measure only the antibiotic sensitivity of the free-floating organisms, rather than organisms in a biofilm state. As a result, a dose of antibiotics is administered to the patient, such as through a catheter, in amounts that rarely have the desired effect on the biofilm phase organisms that may reside in the catheter. The biofilm organisms may continue to shed more planktonic organisms or may go dormant and proliferate later as an apparent recurrent infection.

In order to eradicate biofilm organisms through use of antibiotics, a laboratory must determine the concentration of antibiotic required to kill the specific genetic biofilm phase of the organism. Highly specialized equipment is required to provide the minimum biofilm eradication concentration. Moreover, the current diagnostic protocols are time consuming, and results are often not available for many days, e.g. five (5) days. This time period clearly doesn't allow for prompt treatment of infections. The delay and the well justified fear of infection may result in the overuse of broad-spectrum antibiotics and continued unnecessary catheter removal and replacement procedures. Overuse of broad-spectrum antibiotics can result in the development of antibiotic resistant bacterial strains, which cannot be effectively treated. Unnecessary catheter removal and replacement is painful, costly and may result in trauma and damage to the tissue at the catheter insertion site.

The antibiotic resistance of biofilms, coupled with complications of antibiotic use, such as the risk of antibiotic resistant strains developing, has made antibiotic treatment an unattractive option. As a result, antibiotic use is limited to symptomatic infections and prophylactic antibiotics are not typically applied to prevent contamination. Because the biofilm can act as a selective phenotypic resistance barrier to most antibiotics, the catheter must often be removed in order to eradicate a catheter related infection. Removal and replacement of the catheter is time consuming, stressful to the patient, and complicates the medical procedure. Therefore, there are attempts to provide convenient and effective methods for killing organisms, and especially those dwelling inside of catheters, without the necessity of removing the catheter from the body.

In addition to bacterial and fungal infections, amoebic infections can be very serious and painful, as well as potentially life threatening. Several species of *Acanthameoba*, for example, have been found to infect humans. *Acanthamoeba* are found worldwide in soil and dust, and in fresh water sources as well as in brackish water and sea water. They are frequently found in heating, venting and air conditioner units, humidifiers, dialysis units, and in contact lens paraphernalia. *Acanthamoeba* infections, in addition to microbial and fungal infections, may also be common in connection with other medical and dental devices, including toothbrushes, dentures and other dental appliances, and the like. *Acanthamoeba* infections often result from improper storage, handling and disinfection of contact lenses and other medical devices that come into contact with the human body, where they may enter the skin through a cut, wound, the nostrils, the eye, and the like.

There are numerous different kinds of microbes that present problematic infections, including varieties of bacteria and fungi. However, present methods of eliminating infections are generally limited in the scope of the different microbes that a solution is effective against. "Inhibitory Effect of Disodium EDTA upon the Growth of *Staphylococcus epidermidis* In Vitro: Relation to Infection Prophylaxis of Hickman Catheters", Root, et al., ANTIMICROBIAL AGENTS AND CHEMOTHERAPY, November 1988, p. 1627-1633, describes the in-vitro use of disodium EDTA against a particular catheter-associated *Staphylococcus epidermidis* pathogen isolate.

EDTA has traditionally been useful as a metal chelator and has been used, in combination with other active compounds, for a variety of purposes. EDTA is often used, in low concentrations, as an in-vitro anticoagulant for blood specimen collection and testing and as an antioxidant synergist, and is added to solutions, for example, as a chelator, a stabilizer, or a preservative for pharmaceutical preparations. EDTA may exist in a variety of forms, some of which are sodium salt forms, such as disodium, trisodium, and tetrasodium salts and others metal chelates such as iron, copper, magnesium, etc. Certain forms of EDTA have been utilized, in conjunction with other substances as an adjuvant, in compositions for treating infected catheters. When used in a clinical setting, or in a composition that interacts with humans or animals, the solutions are generally adjusted to a generally physiological, or neutral, pH range.

A combination of an alcohol with an additive, such as a non-sodium salt form of EDTA, is described in PCT Application WO 02/05188. PCT Application, WO 00/72906 A1 describes a lyophilized mixture of an antimicrobial agent, e.g. antibiotic, and a second agent that may be non-sodium salt form of EDTA as a chelating agent for catheter flushing. In U.S. Pat. No. 5,688,516, a composition having an anticoagulant, a chelating agent, such as EDTA and an antimicrobial agent, such as Minocycline, are described for coating medical devices and inhibiting catheter infection. In particular described examples, a disodium form of EDTA is brought to a physiological pH of 7.4 and is used in the composition. PCT Application, WO 99/09997 describes treatment of fungal infection with a combination of an antifungal agent, and a chelator, such as EDTA.

Other areas in which infections present a problem include medical devices and materials used in connection with the eyes, such as contact lenses, scleral buckles, suture materials, intraocular lenses, and the like. In particular, there has been emphasis on discovery of methods to disinfect of ocular prosthesis, e.g. contact lenses. Bacterial biofilms may participate in ocular infections and allowing bacteria to persist on abiotic surfaces that come in contact with, or are implanted in the eye. Biofilms also may form on the biotic surfaces of the eye. "The Role of Bacterial Biofilms in Ocular Infections, DNA CELL BIOL., 21(5-6):415-20, May-June 2002. A severe form of keratitis can also be initiated by a protozoan amoeba which can contaminate lens disinfectant fluids. An ophthalmic formulation of tetrasodium EDTA and alkali salts, buffered to a pH of 6-8 to disinfect contact lenses is described in U.S. Pat. No. 5,300,296. U.S. Pat. No. 5,998,488 describes an opthalmic composition of EDTA and other substances, such as cyclodextrin and boric acid.

In the dental field, items to be placed in a mouth, such as dental tools, dental and orthodontic devices such as retainers, bridges, dentures, and the like need to be maintained in a sterile condition, particularly during storage and prior to placement in the mouth. Otherwise, infection may be transmitted to the bloodstream and become serious. U.S. Pat. No. 6,077,501 describes EDTA used in a denture cleanser composition with other active compositions.

The water supply is also prone to microbial and other types of infections. Water storage devices, as well as water supply and withdrawal conduits, often become infected. The internal surfaces of fluid bearing tubing in medical and dental offices present an environment that is suitable for microbial infection and growth and, in fact, the adherence of microbes and formation of the highly protective biofilm layer is often problematic in fluid storage and supply devices.

There is a need for improved methods and substances to prevent and destroy infections in a variety of environments. Such antiseptic solutions should have a broad range to of antimicrobial properties. In particular, the solutions should be capable of penetrating biofilms to eradicate the organisms comprising the biofilms. The methods and solutions should be safe enough to be use as a preventive measure as well as in the treatment of existing infections.

SUMMARY OF THE INVENTION

The present invention involves antiseptic solutions comprising, or consisting essentially of, or consisting of, one or more salt(s) of EDTA at a prescribed concentration and/or pH. The inventors have discovered, unexpectedly, that certain EDTA compositions and combinations provide powerful antiseptic activities and function as broad-spectrum anti-microbial agents, as well as fungicidal agents against many strains of pathogenic yeast. EDTA compositions and combinations of the present invention are also highly effective in killing pathogenic biofilm organisms and in reducing and eliminating existing biofilms, as well as preventing biofilm formation. EDTA compositions and combinations moreover exhibit anti-protozoan activity and also exhibit anti-amoebic activity. Based on published reports, the EDTA compositions of the present invention are expected to exhibit anti-viral activity.

The EDTA formulations of the present invention are safe for human administration and are biocompatible and non-corrosive. They may also have anticoagulant properties and are thus useful for preventing and/or treating a variety of catheter-related infections. The antiseptic solutions of the present invention have numerous applications, including applications as lock and lock flush solutions for various types of catheters, use as antiseptic agents or solutions for sanitizing a range of medical, dental and veterinary devices, instruments and other objects, surfaces, and the like. They furthermore have sanitizing applications in industrial and food preparation and handling settings.

In one embodiment, antiseptic compositions of the present invention have at least four, and preferably at least five, of the following properties: anticoagulant properties; inhibitory and/or bactericidal activity against a broad spectrum of bacteria in a planktonic form; inhibitory and/or fungicidal activity against a spectrum of fungal pathogens; inhibitory and/or bactericidal activity against a broad spectrum of bacteria in a sessile form; inhibitory to activity against protozoan infections; inhibitory activity against *Acanthamoeba* infections; safe and biocompatible, at least in modest volumes, in contact with a patient; safe and biocompatible, at least in modest volumes, in a patient's bloodstream; and safe and compatible with industrial objects and surfaces.

Methods for inhibiting the growth and proliferation of microbial populations and/or fungal pathogens, including inhibiting the formation and proliferation of biofilms, are provided that comprise contacting an infected or suspected infected object, or surface, with a sanitizing composition of the present invention. Methods for inhibiting the growth and proliferation of protozoan populations are provided, comprising contacting an infected or suspected infected object, or surface, with a sanitizing composition of the present invention. Methods for inhibiting the growth and proliferation of amoebic populations, and for preventing amoebic infection, particularly *Acanthamoeba* infections, are provided, comprising contacting an object, or a surface, with a sanitizing composition of the present invention.

Methods for substantially eradicating microbial populations, including both planktonic microbial populations and microbial populations in the form of biofilms, are also provided and comprise contacting an infected or suspected infected object, or surface, with a sanitizing composition of the present invention. Methods for substantially eradicating an *Acanthamoeba* population are provided and comprise contacting an infected or suspected infected object, or surface, with a sanitizing composition of the present invention. Depending on the antiseptic composition used in the various methods, various compositions and contact time periods may be required to inhibit the formation and proliferation of various populations, and/or to substantially eradicate various populations. Suitable contact time periods for various compositions are provided in the examples and may be determined by routine experimentation.

Soluble salts of EDTA are used in compositions of the present invention. Sodium salts of EDTA are commonly available and generally used, including di-sodium, tri-sodium and tetra-sodium salts, although other EDTA salts, including ammonium, di-ammonium, potassium, di-potassium, cupric di-sodium, magnesium di-sodium, ferric sodium, and combinations thereof, may be used, provided they have the antibacterial and/or fungicidal and/or anti-protozoan and/or anti-amoebic properties desired, and provided that they are sufficiently soluble in the solvent desired. Various combinations of EDTA salts may be used and may be preferred for particular applications. Importantly, in most embodiments, sanitizing compositions and methods of the present invention do not employ traditional antibiotic agents and thus do not contribute to the development of antibiotic resistant organisms.

In one embodiment, antiseptic compositions consisting of, consisting essentially of, or comprising one or more sodium salt(s) of EDTA at a pH higher than physiological pH are provided as antiseptic compositions of the present invention. Such antiseptic compositions have application as lock solutions and lock flush solutions for various types of in-dwelling access catheters, including vascular catheters used for delivery of fluids, blood products, drugs, nutrition, withdrawal of fluids or blood, dialysis, monitoring of patient conditions, and the like. Antiseptic solutions of the present invention may also be used as lock and lock flush solutions for urinary catheters, nasal tubes, throat tubes, and the like. The general solution parameters described below are suitable for these purposes. In one embodiment, an antiseptic solution consisting of, consisting essentially of, or comprising one or more sodium EDTA salt(s) at a pH higher than physiological pH is provided to maintain the patency of in-dwelling intravascular access devices. Methods for sanitizing catheters and other medical tubes, such as nasal tubes, throat tubes, and the like, are also provided and involve contacting the catheter or other medical tube with a sanitizing composition of the present invention.

In another embodiment, antiseptic compositions of the present invention consisting of, consisting essentially of, or comprising one or more sodium salt(s) of EDTA at a pH greater than physiological pH are provided as sanitizing solutions for medical devices such as dentures and other dental and/or orthodontic and/or periodontal devices, for contact lenses and other optical devices, for medical and veterinary instruments, devices, and the like, and as sanitizing solutions for sanitizing surfaces and objects. Methods of sanitizing such devices are also provided, the methods comprising contacting a device with antiseptic compositions of the present invention. In general, antiseptic compositions of the present invention may be used as soaking solutions for dental, orthodontic and periodontal devices, including toothbrushes, and are also used as soaking solutions for contact lenses and other optical devices, and well as medical and veterinary instruments, devices, and the like. For these applications, antiseptic compositions of the present invention are generally formulated as solutions, or are provided in a dry form which, upon introduction of a suitable solvent, forms a solution.

In yet another embodiment, antiseptic compositions of the present invention are formulated for use in solutions, gels, creams and other preparations designed for topical use as antiseptic agents, wipes, antibacterial treatments, and the like. Antiseptic compositions of the present invention may also be used as anti-bacterial agents in connection with bandages, dressings, wound healing agents and devices, and the like.

In still another embodiment, antiseptic compositions of the present invention are used in industrial settings such as water storage and distribution systems, water purification, humidification and dehumidification devices, and in food preparation, handling and packaging settings to inhibit, reduce or substantially eliminate microbial populations in both planktonic and sessile forms, as well as many fungal, amoebic and planktonic populations. Industrial equipment and surfaces may be contacted or flushed with, or soaked in antiseptic compositions of the present invention. Time release antiseptic composition formulations may also be provided to provide treatment over time, particularly in locations that are difficult to access frequently.

BRIEF DESCRIPTION OF THE DRAWINGS

FIGS. 1A-1D show minimum inhibitory concentration (MIC) and minimum bactericidal (MBC) concentrations for various gram-positive and gram-negative bacterial organisms against EDTA salt solutions consisting essentially of di-potassium EDTA; di-ammonium EDTA; di-sodium EDTA; tri-sodium EDTA and tetra-sodium EDTA, using the agar dilution method. The bacterial organisms were isolated from catheter-related infections in human patients. Experimental techniques are described in Example 1.

FIG. 2 shows MIC and MBC concentrations for various fungal organisms against different formulations of EDTA, using the agar dilution method. Experimental techniques are described in Example 1. The fungal organisms were collected from human patient samples.

FIGS. 3A and 3B show MIC and MBC data for gram-positive and grain-negative bacterial organisms against EDTA salt solutions consisting essentially of: cupric di-sodium EDTA; magnesium di-sodium EDTA and ferric sodium EDTA. The bacterial organisms were isolated from catheter-related infections in human patients. Experimental techniques are described in Example 1.

FIGS. 4A-4C show MIC and MBC data for various gram-positive and gram-negative bacterial organisms against combination EDTA salt solutions consisting essentially of: cupric di-sodium and tetra-sodium EDTA; cupric di-sodium and di-potassium EDTA and cupric di-sodium and di-ammonium EDTA. The bacterial organisms were, isolated from catheter-related infections in human patients. Experimental techniques are described in Example 1.

FIGS. 5A-5C show MIC and MBC data for various gram-positive and gram-negative bacterial organisms against combination EDTA salt solutions consisting essentially of: tetra-sodium and di-ammonium EDTA; tetra-sodium and di-potassium EDTA; and di-ammonium and di-potassium EDTA. The bacterial organisms were isolated from catheter-related infections in human patients. Experimental techniques are described in Example 1.

FIG. 6 shows the minimum biofilm eradication concentration (MBEC) values for various organisms, expressed in mg/ml tetra-sodium EDTA (w/v) using the methodology described in Example 2.

FIG. 7 shows experimental results produced by treating infected renal hemodialysis catheters with an antiseptic composition consisting essentially of tetra-sodium EDTA at a concentration of 40 mg/ml (w/v).

FIG. 8 shows experimental results produced by treating infected renal hemodialysis catheters, as well as one arterial and one venous catheter, with an antiseptic composition consisting essentially of tetra-sodium EDTA at concentrations of 20-100 mg/ml (w/v).

DETAILED DESCRIPTION OF THE INVENTION

EDTA is used at low concentrations in many compositions, in combination with other active components, as a stabilizer or preservative agent. Antiseptic compositions of the present invention comprise generally higher concentrations of EDTA and preferably comprise at least 1.0% EDTA salt(s), by weight per volume of solution (w/v), and may comprise up to 15% (w/v) EDTA salt(s). Antiseptic compositions comprising at least 2.0% (w/v) EDTA salt(s) and less than 10% (w/v) EDTA salt(s) are preferred for many applications. Antiseptic compositions comprising between 2.0% (w/v) EDTA salt(s) and 8.0% (w/v) EDTA salt(s) are preferred for many applications, and compositions comprising between 2.0% and 6.0% EDTA salt(s) are especially preferred for many applications. Exemplary compositions, described below, comprise 3.6-4.4% (w/v) EDTA salt(s) in aqueous solution.

The desired EDTA salt(s) concentration for various applications may depend on EDTA salt(s) or combination of salts employed, the type of infection being treated and, to some degree, on the solvent used for antiseptic compositions. When aqueous solvents comprising ethanol are used, for example, the concentration of EDTA salt(s) required to provide the desired level of activity may be reduced compared to the EDTA salt(s) concentration used in compositions having water as the solvent. Antiseptic compositions comprising one or more EDTA salt(s) have demonstrated inhibitory and/or bactericidal efficacy at concentration ranges of 0.5% to 30% or more, as shown in the exemplary data provided below. "Effective" concentrations of desired EDTA salt(s) in antiseptic compositions of the present invention for inhibitory, bactericidal, fungicidal, biofilm eradication and other purposes, may be determined by routine experimentation, as described in the examples provided below.

The British Pharmacopoeia (BP) specifies that a 5% solution of di-sodium EDTA has a pH of 4.0 to 5.5. The BP also specifies a pH range of 7.0 to 8.0 for solutions of tri-sodium EDTA. The pH values for other EDTA salts in aqueous solution are shown in Example 10, below. At physiological pH, the sodium salts of EDTA exist as a combination of di-sodium and tri-sodium EDTA, with the tri-sodium salt of EDTA being predominant. In the U.S., pharmaceutical "di-sodium" EDTA prepared for injection has generally been titrated with sodium hydroxide to a pH of 6.5 to 7.5. At this pH, the EDTA solution actually comprises primarily tri-sodium EDTA, with a lesser proportion of the di-sodium salt. Other compositions comprising sodium salts of EDTA that are used in medical or healthcare applications are generally adjusted to a pH that is substantially physiological.

In certain embodiments, antiseptic compositions of the present invention comprise, or consist essentially of, or consist of, a sodium EDTA salt (or combination of sodium EDTA salts) in solution at a pH higher than physiological, preferably at a pH of >8.0, or at a pH >8.5, or at a pH>9, or at a pH>9.5. In another embodiment, antiseptic compositions of the present invention comprise, or consist essentially of, or consist of, a sodium EDTA salt (or combination of sodium salts) in solution at a pH in the range between 8.5 and 12.5 and, in another embodiment, at a pH of between 9.5 and 11.5 and, in yet another embodiment, at a pH of between 10.5 and 11.5. When used herein, the term "EDTA salt" may refer to a single salt, such as a di-sodium or tri-sodium or tetra-sodium salt, or another EDTA salt form, or it may refer to a combination of such salts. The composition of EDTA salt(s) depends both on the EDTA salts used to formulate the composition, and on the pH of the composition. For antiseptic compositions of the present invention comprising sodium EDTA salt(s), and at the desired pH ranges (specified above), the sodium EDTA salts are predominantly present in both the tri-sodium and tetra-sodium salt forms.

In one embodiment, antiseptic compositions of the present invention comprise, or consist essentially of, a combination of at least the tri-sodium and tetra-sodium salts of EDTA. In another embodiment, antiseptic compositions of the present invention comprise, or consist essentially of, a combination of at least the tri-sodium and tetra-sodium salts of EDTA, in which at least 10% of the EDTA in the composition is present in the tetra-sodium salt form. In yet another embodiment, antiseptic compositions of the present invention comprise, or consist essentially of, a combination of at least tri-sodium and tetra-sodium salts of EDTA, in which at least 50% and, in another embodiment, at least 60%, of the EDTA in the composition is present in the tri-sodium salt form. In another embodiment, antiseptic compositions of the present invention comprise, or consist essentially of, a combination of di-sodium and tri-sodium and tetra-sodium EDTA, in which less than 10% of the EDTA in the composition is present in the di-sodium salt form.

Antiseptic compositions comprising, or consisting essentially of, or consisting of EDTA salt(s) other than or in addition to sodium EDTA salts have different "effective" pH ranges. "Effective" pH ranges for desired EDTA salt(s) in antiseptic compositions of the present invention for inhibitory, bactericidal, fungicidal, biofilm eradication and other purposes, may be determined by routine experimentation.

In some embodiments, antiseptic compositions of the present invention consist of the EDTA salt(s), as described above, and antiseptic solutions consist of EDTA salts dissolved in a solvent, generally an aqueous solvent such as water or saline. In other embodiments, antiseptic compositions of the present invention consist essentially of the EDTA salt(s), as described above, generally in an aqueous solvent such as water or saline. Antiseptic compositions of the present invention consisting essentially of an EDTA salt or a combination of EDTA salts are substantially free from other active substances having substantial antimicrobial and/or anti-fungal activity. Substantial antimicrobial and/or anti-fungal activity, in this context, means anti-microbial and/or antifungal activity that is at least 50% of the anti-microbial and/or antifungal activity of a sodium EDTA salt(s) composition in aqueous solution at a concentration of 4.0% (w/v) at a pH of 10.5.

In some embodiments, antiseptic compositions of the present invention comprise EDTA salt(s) having specified concentration(s), at specified pH ranges, and may contain materials, including active components, in addition to the EDTA salts described above. Other antimicrobial or biocidal components may be incorporated in antiseptic compositions of the present invention comprising EDTA salt(s), although the use of traditional antibiotics and biocidal agents is generally discouraged as a consequence of the dire consequences of the development of antibiotic- and biocidal-resistant organisms. In some embodiments, antiseptic compositions of the present invention comprising EDTA salt(s) having specified concentration(s), at specified pH ranges, are substantially free from other active substances having substantial antimicrobial and/or anti-fungal activity.

Other active and inactive components may also be incorporated in antiseptic compositions of the present invention comprising EDTA salt(s), provided that they don't deleteriously affect the activity and/or stability of the EDTA salt(s). Proteolytic agents may be incorporated in antiseptic compositions for some applications. Antiseptic compositions formulated for topical application have various creams, emoluments, skin care compositions such as aloe vera, and the like, for example. Antiseptic compositions of the present invention provided in a solution formulation may also comprise other active and inactive components, provided they don't interfere, deleteriously, with the activity and/or stability of the EDTA salt(s).

The compositions of the present invention may be used in a solution or a dry form. In solution, the EDTA salt(s) are preferably dissolved in a solvent, which may comprise an aqueous solution, such as water or saline, or another biocompatible solution in which the EDTA salt(s) are soluble. Other solvents, including alcohol solutions, may also be used. In one embodiment, EDTA salt compositions of the present invention are formulated in a mixture of water and ethanol. Such solutions are highly efficacious and may be prepared by making a concentrated EDTA salt(s) stock solution in water and then introducing the desired concentration of ethanol. EDTA salt concentrations of from about 1.0 to 10. %, w/v, are suitable, and ethanol concentrations of from more than about 0.5% and less than about 10%, v/v, provide effective antiseptic compositions. In some embodiments, EDTA salt concentrations of about 2.0% (w/v) in water with an ethanol concentration of about 1% (v/v) are highly effective against a broad spectrum of bacterial strains. When sodium EDTA salts are used, the pH ranges of these antiseptic compositions are as described above. Bio-compatible non-aqueous solvents may also be employed, provided the EDTA salt(s) can be solubilized and remain in solution during storage and use.

EDTA solutions of the present invention are preferably provided in a sterile and non-pyrogenic form and may be packaged in any convenient fashion. In some embodiments, antiseptic EDTA compositions of the present invention may be provided in connection with or as part of a medical device, such as in a pre-filled syringe or another medical device. The compositions may be prepared under sterile, aseptic conditions, or they may be sterilized following preparation and/or packaging using any of a variety of suitable sterilization techniques. Single use vials, syringes or containers of EDTA solutions may be provided. Multiple use vials, syringes or containers may also be provided. Systems of the present invention include such vials, syringes or containers containing the EDTA solutions of the present invention.

The compositions of the present invention may also be provided in a substantially "dry" form, such as a substantially dry coating on a surface of tubing, or a conduit, or a medical or industrial device such as a catheter or conduit, or a container, or the like. Such substantially dry forms of EDTA compositions of the present invention may be provided in a powder or lyophilized form that may be reconstituted to form a solution with the addition of a solvent. Substantially dry forms of EDTA compositions may alternatively be provided as a coating, or may be incorporated in a gel or another type of carrier, or encapsulated or otherwise packaged and provided on a surface as a coating or in a container. Such substantially dry forms of EDTA compositions of the present invention are formulated such that in the presence of a solution, the substantially dry composition forms an EDTA solution having the composition and properties described above. In certain embodiments, different encapsulation or storage techniques may be employed such that effective time release of the EDTA is accomplished upon extended exposure to solutions. In this embodiment, the substantially dry EDTA solutions may provide antiseptic activity over an extended period of time and/or upon multiple exposures to solutions.

Compositions comprising EDTA have a well established safety profile in connection with medical usage and administration to humans. Doses of up to 3000 mg EDTA disodium are infused over 3 hours, on a daily basis, for the treatment of hypercalcemia in humans. This dose is well tolerated. EDTA salts are also present, in combination with other components, in many solutions used in medical and human health applications, and have been established as safe for human use, both in vitro and in vivo. EDTA salts are readily available at a reasonable cost, and are stable over time in solution.

Formulation and production of antiseptic compositions of the present invention is generally straightforward. In one embodiment, desired antiseptic compositions of the present invention are formulated by dissolving one or more EDTA salt(s) in an aqueous solvent, such as purified water, to the desired concentration and adjusting the pH of the EDTA salt solution to the desired pH. In alternative embodiments, desired antiseptic compositions of the present invention are formulated by dissolving one or more EDTA salt(s) in a solvent in which the EDTA salt or combination of salts is soluble to provide a concentrated, solubilized EDTA salt solution, and additional solvents or components may then be added, or the solubilized EDTA salt composition may be formulated in a form other than a solution, such as a topical preparation. The antiseptic solution may then be sterilized using conventional means, such as autoclaving, UV irradiation, filtration and/or ultrafiltration, and other means. The preferred osmolarity range for EDTA solutions is from 240-500 mOsM/Kg, more preferably from 300-420 mOsm/Kg. The solutions are preferably formulated using USP materials.

Antiseptic compositions consisting of, or consisting essentially of, or comprising tri- or tetra-sodium salt(s), or a mixture of tri- and tetra-sodium salts, are preferred for many applications and may be prepared using sodium salts of EDTA other than tri- and tetra-sodium salts, such as di-sodium EDTA, which is readily available. Di-sodium EDTA solutions have a lower pH in solution than the desired pH range of compositions of the present invention but, upon pH adjustment to the desired range using a pH adjustment material, such as sodium hydroxide, sodium acetate, and other well-known pH adjustment agents, EDTA solutions prepared using di-sodium salts are converted to the preferred combination di- and/or tri- and/or tetra-sodium salt EDTA compositions of the present invention. Thus, different forms and combinations of EDTA salts may be used in the preparation of EDTA compositions of the present invention, provided that the pH of the composition is adjusted to the desired pH range prior to use. In one embodiment, antiseptic compositions consisting of a mixture of primarily tri- and tetra-sodium EDTA is provided by dissolving di-sodium EDTA in an aqueous solution, 3%-5% on a weight/volume basis, and adding sodium hydroxide in a volume and/or concentration sufficient to provide the desired pH of >8.5 and <12.0.

Antiseptic compositions of the present invention comprising, or consisting essentially of, or consisting of, EDTA salt(s) as described above are also useful for many other applications. EDTA solutions may be used as antiseptic solutions for soaking, or rinsing, or contacting medical, dental and veterinary surfaces and objects. EDTA solutions of the present invention may be used, for example, for storing and/or sanitizing contact lenses and other optical devices; for storing and/or sanitizing dental devices such as dentures, bridges, retainers, tooth brushes, and the like, and for storing and/or sanitizing medical and dental and veterinary devices and instruments. In these applications, the devices or surfaces may be contacted with EDTA solutions of the present invention for a time sufficient to substantially eliminate microbial and/or fungicidal infections, or devices and surfaces may be soaked in EDTA solutions for a desired time period. EDTA compositions of the present invention may additionally be used to sanitize water and other fluid supply lines. Sanitizing of fluid supply lines may be accomplished by intermittently flushing the lines with EDTA compositions of the present invention. Similarly, EDTA compositions of the present invention may be used to eradicate biofilms and microbial (including some virus and protozoa) and fungal populations in water supply and storage devices.

Numerous experimental tests and procedures have been carried out using EDTA containing compositions of the present invention to establish their properties and their efficacy as antiseptic compositions. Several experimental procedures are described in detail below. These procedures and the experimental results are being provided for illustrative purposes only and are not intended to limit the scope of the present invention in any way.

Example 1

Minimum Inhibitory Concentration (MIC) and Minimum Bactericidal Concentration (MBC) Data for Organisms Against Different Formulations of EDTA, Using the Agar Dilution Method The minimum inhibitory concentrations (MIC) and minimum bactericidal concentrations (MBC) for various gram-positive and gram-negative bacterial and yeast organisms were established for several different formations of EDTA. The MICs and MBCs for various organisms were also tested in combinations of EDTA salt(s). The agar dilution method (protocol described below) was used.

The gram-positive and gram-negative bacterial organisms were isolated from human patients having catheter-related infections to ensure that the bacterial stains were actively pathogenic and were of the type common in human catheter-related bacterial infections. The yeast organisms were collected from patients having serious septicemic infections. The organisms were catalogued and maintained in the laboratory of Peter Kite at the University of Leeds.

Various EDTA salt solutions and combination EDTA salt solutions were prepared by dissolving relevant reagent grade EDTA salts in distilled water to the desired EDTA salt concentration (w/v). Concentrated stock EDTA salt solutions were prepared for each EDTA salt or EDTA salt combination for determining the MIC and MBC for various organisms. Tetra- and tri-sodium EDTA solutions were prepared using the tetra- and tri-sodium salts of EDTA rather than using di-sodium EDTA and adjusting the pH of the solution to achieve the desired pH ranges. EDTA salt solutions were sterilized prior to use and stored at 4° C.

Agar Dilution Method Protocol
Making the Agar
  Place 2 liters of nutrient agar into a steam bath and leave for about 1 hour (until molten).
  Allow the agar to cool to 50° C.
  Collect 20 sterile (125 mL) glass bottles and allocate 100 mL of the nutrient agar to each one. To this
  add 0.5, 1.0, 1.5, 2.0, 4, 6, 8, 10, 15, 20, 25, 30, 40, 50, 60, 70, 80, 90 and 100 mg/mL of Tetra-sodium EDTA (or other EDTA salt or EDTA salt combination being tested), using a stock solution at 200 mg/mL.
  Pour 20 mL agar into a sterile petri dish and allow to set. Pour 3 further plates. Label the plates with the concentration of EDTA they contain. Do this for each concentration.
  These plates can then be stored, until they are needed, in a 4° C. fridge.
Inoculating the Plates
  Grow overnight cultures of 23 Gram-positive organisms and 19 Gram-negative organisms in nutrient broth.
  Dilute each culture to $10^6$ cfu/mL, using Phosphate buffered saline (PBS).
  Use an automatic plate inoculator to inoculate each plate with 21 organisms.
  Incubate the plates overnight at 37° C.
  Next day score + or − for growth.
  Use sterile filter paper to transfer the growth from the initial plates to fresh Cled agar plates to
  determine the MBC's.
  Incubate the replica plates overnight at 37° C.
  Next day score + or − for growth. The MIC and MBC were described as, the lowest concentration at which there was no growth.

Results are shown in FIGS. 1A-5C. FIGS. 1A-1D show MIC and MBC data (presented as mg/ml EDTA solution, w/v) for many gram-positive and gram-negative organisms against EDTA salt solutions consisting essentially of di-potassium EDTA; di-ammonium EDTA; di-sodium EDTA; tri-sodium EDTA and tetra-sodium EDTA. FIG. 2 shows MIC and MBC data (presented as mg/ml EDTA solution w/v) for yeasts against EDTA salt solutions consisting essentially of: tetra-sodium EDTA; di-potassium EDTA; and di-ammonium EDTA.

FIGS. 3A and 3B show MIC and MBC data (presented as mg/ml EDTA solution, w/v) for gram-positive and gram-negative organisms against EDTA salt solutions consisting essentially of: cupric di-sodium EDTA; magnesium di-sodium EDTA and ferric sodium EDTA.

FIGS. 4A-4C show MIC and MBC data (presented as mg/ml EDTA solution, w/v) for gram-positive and gram-negative organisms against combination EDTA salt solutions consisting essentially of: cupric di-sodium and tetra-sodium EDTA; cupric di-sodium and dipotassium EDTA; and cupric di-sodium and di-ammonium EDTA.

FIGS. 5A-5C show MIC and MBC data (presented as mg/ml EDTA solution, w/v) for gram-positive and gram-negative organisms against combination EDTA salt solutions consisting essentially of: tetra-sodium and di-ammonium EDTA; tetra-sodium and dipotassium EDTA; and di-ammonium and di-potassium EDTA.

Several of the EDTA salts and EDTA salt combinations were effective in inhibiting and/or eliminating a broad spectrum of bacterial strains at reasonable concentrations. Prior medical testing and use has established good biocompatibility profiles for the use of sodium EDTA salts in humans and animals, while the biocompatibility of other EDTA salts has not yet been established. Tetra- and tri-sodium EDTA salts appeared to be the most efficacious against a broad spectrum of pathogenic bacteria, they have been or could easily be established to be biocompatible for human and veterinary use, and they are cost effective and stable. Tetra-sodium EDTA salt is additionally active as an anticoagulant and is highly soluble in aqueous solvents. Based on these factors and the experiments outlined above, tetra- and tri-sodium EDTA salts were chosen as the most promising candidates for antiseptic compositions of the present invention.

Example 2

Minimum Biofilm Eradication (MBEC) Data for Organisms Against Tetra-Sodium EDTA, using the Modified Calgary Method Biofilm formation is an important factor in bacterial contamination. An effective antiseptic composition preferably has the ability to reduce the proliferation of biofilm, or prevent or inhibit the formation of biofilms. We therefore tested our candidate tetra-sodium EDTA antiseptic solution to determine whether it could prevent or inhibit the formation of biofilms. The minimum biofilm eradication concentration (MBEC) for various organisms against tetra-sodium EDTA was established using a modified Calgary device method. The Calgary method is described in the CANADIAN JOURNAL OF VETERINARY RESEARCH, 66:8692 (2002) and in U.S. Pat. No. 6,599,714. The method and results are described below.

Tetra-sodium EDTA salt solutions were prepared by dissolving reagent grade tetra-sodium EDTA salt in distilled water to the desired EDTA salt concentration (w/v).

Concentrated stock tetra-sodium EDTA salt solutions were prepared for determining the MBEC for various organisms in a sessile or biofilm form. Tetra-sodium EDTA solutions were sterilized prior to use and stored at 4° C.

Method

Forming Biofilm:
- Use 100 mL of Muller Hinton overnight broth of required organism.
- Pipette 200 uL into all the wells in a 96 well microtitre tray. Place on lid with 96 pins. Incubate on an orbital shaker for 24 hours at 37° C. at a speed of 200 rpm.

Susceptibility Test:
- Use biofilm formed above.
- Place lid (with pins) into a new 96 well microtitre tray containing 250 uL of required concentrations of test agent. Incubate for 1 to 24 hours at 37° C. (Not on shaker).
- At time intervals of 1, 3, 6, and 24 hours, remove 4 pins for each concentration from the lid by inserting a screwdriver and snapping pin off into the well.
- Place 3 pins for each concentration into a 5 ml wash of PBS and invert once.
- Place the three pins into 3 mL of PBS and sonicate for 15 minutes. Plate out 2 uL onto 3×CLED plates and spread using a sterile plastic spreader. Incubate at 37° C. overnight. Read colony counts next day.
- Place the remaining loose pin (for each concentration) into 600 uL of 4% formal saline for SEM.

The MBEC values for various organisms, expressed in mg/ml tetra-sodium EDTA (w/v) determined using this method, are shown in FIG. 6. The results demonstrate that 40 mg/ml tetra-sodium EDTA (4% w/v) was an effective biofilm eradication concentration for all microbial populations tested.

Exemplary data generated by MBEC experiments for various microorganisms are provided below. Tetra-sodium EDTA was used for all experiments, which were performed in triplicate.

| Organism: 250 E. coli | | | | |
|---|---|---|---|---|
| Conc. EDTA mg/mL | Colony count/mL after 1 hour | Colony count/mL after 3 hours | Colony count/mL after 6 hours | Colony count/mL after 24 hours |
| 0 | 40152 | 53285 | 64234 | 6133 |
|   | 48175 | 62044 | 56934 | 4960 |
|   | 43796 | 61314 | 76642 | 5120 |
| 5 | 0 | 520 | 80 | 0 |
|   | 0 | 540 | 80 | 0 |
|   | 0 | 620 | 133 | 730 |
| 10 | 0 | 0 | 0 | 0 |
|    | 0 | 0 | 0 | 0 |
|    | 0 | 0 | 0 | 0 |
| 15 | 0 | 0 | 0 | 0 |
|    | 0 | 0 | 0 | 0 |
|    | 0 | 0 | 0 | 0 |
| 20 | 0 | 0 | 0 | 0 |
|    | 0 | 0 | 0 | 0 |
|    | 0 | 0 | 0 | 0 |

For 250 E. coli, the MBEC = 10 mg/mL tetra-sodium EDTA.

| Organism: J26 Pseudomonas aeruginosa | | | | |
|---|---|---|---|---|
| Conc. EDTA mg/mL | Colony count/mL after 1 hour | Colony count/mL after 3 hours | Colony count/mL after 6 hours | Colony count/mL after 24 hours |
| 0 | 86861 | 4400 | 92701 | 66667 |
|   | 89781 | 3060 | 79562 | 35036 |
|   | 94891 | 3080 | 83212 | 41606 |
| 5 | 0 | 0 | 0 | 0 |
|   | 0 | 0 | 0 | 0 |
|   | 0 | 0 | 0 | 0 |
| 10 | 0 | 0 | 0 | 0 |
|    | 0 | 0 | 0 | 0 |
|    | 0 | 0 | 0 | 0 |
| 15 | 0 | 0 | 0 | 0 |
|    | 0 | 0 | 0 | 0 |
|    | 0 | 0 | 0 | 0 |
| 20 | 0 | 0 | 0 | 0 |
|    | 0 | 0 | 0 | 0 |
|    | 0 | 0 | 0 | 0 |

For J26 Pseudomonas aeruginosa, the MBEC = <5 mg/mL tetra-sodium EDTA.

| Organism: 292 Enterobacter cloacae | | | | |
|---|---|---|---|---|
| Conc. EDTA mg/mL | Colony count/mL after 1 hour | Colony count/mL after 3 hours | Colony count/mL after 6 hours | Colony count/mL after 24 hours |
| 0 | 1.00E+06 | 103704 | 94444 | 91241 |
|   | 1.00E+06 | 118519 | 131481 | 116667 |
|   | 1.00E+06 | 107407 | 100000 | 131481 |
| 5 | 69343 | 35036 | 36496 | 0 |
|   | 67153 | 15974 | 32197 | 0 |
|   | 67153 | 19697 | 39416 | 0 |
| 10 | 38686 | 12035 | 80 | 0 |
|    | 42336 | 17803 | 219 | 0 |
|    | 40909 | 18561 | 0 | 0 |
| 15 | 8000 | 8133 | 379 | 0 |
|    | 8533 | 8133 | 219 | 0 |
|    | 7467 | 8267 | 133 | 0 |
| 20 | 13786 | 2840 | 0 | 0 |
|    | 12473 | 2820 | 0 | 0 |
|    | 14661 | 2600 | 0 | 0 |

For 292 Enterobacter cloacae, the MBEC = <5 mg/mL tetra-sodium EDTA.

| Organism: H Enterococcus sp. | | | | |
|---|---|---|---|---|
| Conc. EDTA mg/mL | Colony count/mL after 1 hour | Colony count/mL after 3 hours | Colony count/mL after 6 hours | Colony count/mL after 24 hours |
| 0 | 5600 | 3520 | 4000 | 6133 |
|   | 8133 | 3980 | 3440 | 4720 |
|   | 6800 | 3920 | 3760 | 4640 |

-continued

| Organism: H Enterococcus sp. | | | | |
|---|---|---|---|---|
| Conc. EDTA mg/mL | Colony count/mL after 1 hour | Colony count/mL after 3 hours | Colony count/mL after 6 hours | Colony count/mL after 24 hours |
| 5 | 1380 | 780 | 80 | 0 |
|  | 1160 | 580 | 100 | 0 |
|  | 1140 | 500 | 120 | 0 |
| 10 | 40 | 0 | 0 | 0 |
|  | 100 | 0 | 0 | 0 |
|  | 20 | 0 | 0 | 0 |
| 15 | 40 | 0 | 20 | 0 |
|  | 0 | 0 | 0 | 0 |
|  | 80 | 0 | 20 | 0. |
| 20 | 1480 | 730 | 160 | 0 |
|  | 1560 | 379 | 160 | 0 |
|  | 2000 | 320 | 140 | 0 |

For H. *Enterococcus* sp., the MBEC = <5 mg/mL tetra-sodium EDTA.

| Organism J22 Enterobacter cloacae | | | | |
|---|---|---|---|---|
| Conc. EDTA mg/mL | Colony count/mL after 1 hour | Colony count/mL after 3 hours | Colony count/mL after 6 hours | Colony count/mL after 24 hours |
| 0 | 124074 | 107407 | 105556 | 101852 |
|  | 116667 | 91241 | 105556 | 120370 |
|  | 112963 | 98540 | 92701 | 100000 |
| 5 | 6400 | 267 | 2040 | 0 |
|  | 5200 | 133 | 2160 | 0 |
|  | 8933 | 379 | 1820 | 0 |
| 10 | 3540 | 1920 | 267 | 80 |
|  | 3040 | 2900 | 160 | 1532 |
|  | 3760 | 2340 | 219 | 800 |
| 15 | 2620 | 1560 | 740 | 0 |
|  | 2100 | 1740 | 720 | 0 |
|  | 2720 | 1580 | 920 | 0 |
| 20 | 2040 | 80 | 960 | 0 |
|  | 2360 | 1460 | 840 | 0 |
|  | 1620 | 133 | 560 | 0 |

For J22 *Enterobacter cloacae*, the MBEC = 15 mg/mL tetra-sodium EDTA.

| Organism: R81 Proteus vulgaris | | | | |
|---|---|---|---|---|
| Conc. EDTA mg/mL | Colony count/mL after 1 hour | Colony count/mL after 3 hours | Colony count/mL after 6 hours | Colony count/mL after 24 hours |
| 0 | 62044 | 81752 | 112963 | 59259 |
|  | 55474 | 73723 | 103704 | 68519 |
|  | 54015 | 78832 | 107407 | 59124 |
| 5 | 3160 | 160 | 3460 | 0 |
|  | 4000 | 400 | 3120 | 0 |
|  | 4000 | 160 | 3140 | 0 |
| 10 | 1520 | 730 | 400 | 0 |
|  | 1920 | 533 | 1460 | 0 |
|  | 1900 | 438 | 160 | 0 |
| 15 | 2960 | 379 | 1100 | 0 |
|  | 2580 | 80 | 780 | 0 |
|  | 2560 | 400 | 1220 | 0 |
| 20 | 4560 | 400 | 1520 | 0 |
|  | 4480 | 320 | 1280 | 0 |
|  | 2820 | 240 | 720 | 0 |

For R81 *Proteus vulgaris*, the MBEC = <5 mg/mL tetra-sodium EDTA.

Example 3

In Vitro Catheter Lock Treatment Procedure on Patient Positive Catheters

A catheter lock treatment procedure using the candidate 40 mg/ml (4% w/v) tetra sodium EDTA solution was developed and used for sample patient hemodialysis catheters that tested positive for various microbial infections. Catheters that were determined to have microbial infections were subjected to the catheter lock treatment using tetra-sodium EDTA and colony counts were taken at various time points. In a first experiment, all catheters were treated with a 4% w/v tetra-sodium EDTA solution while in a second experiment, catheters were treated with tetra-sodium EDTA solutions at various concentrations. Tetra-sodium EDTA solutions were prepared and stored as described above with reference to Examples 1 and 2. The procedure and results are described below.

Method

Renal hemodialysis catheters removed on suspicion of infection were screened, by flushing 1 mL of sterile Phosphate buffed saline down each lumen. Quantitative culture was performed using 1 and 10 uL aliquots spread onto blood agar plates and incubated.

The catheters were initially stored at 4° C. until after screening and the external lumen sterilized with an alcohol wipe.

Prior to lock treatment testing, the screened positive catheters were locked with nutrient broth using a 5 mL syringe and incubated overnight at 37° C. to ensure biofilm viability and to ensure total colonization of all the endoluminal surfaces with the infecting organism.

After overnight incubation each catheter lumen was flushed with 5 mL of sterile saline and 2×1 cm pieces were cut from the distal end, each placed in 1 mL of 1M sterile calcium chloride, (for neutralization of agent) one for Scanning electron microscopy (SEM) and the other for culture, in sterile universal containers.

For the culture procedure the universal was placed in a sonication bath for 15 mins at room temperature and then vortexed for 20 secs.

Quantitative culture was performed using aliquots of 1 ul and 10 ul plated on blood agar plates and spread by means of sterile plastic L shaped rods, incubated at 37° C. overnight, and colonies counted next day.

The catheter was flushed and locked with the appropriate concentration of tetra-sodium EDTA lock fluid and incubated at 37° C. for 18 hrs.

At 3, 6 and 18 hrs incubation 2×1 cm pieces of the distal end of the catheter were cut off and neutralised in 1 mL of 1M sterile calcium chloride solution.

The quantitative count procedure was followed, at each time interval, as previously described and one piece retained for SEM.

Seventeen (17) infected renal hemodialysis catheters were treated with an antiseptic composition consisting of tetra-sodium EDTA at a concentration of 40 mg/ml (4% w/v). The results are shown in FIG. 7. Ten (10) additional infected renal hemodialysis catheters, as well as one arterial and one venous catheter were treated with an antiseptic composition consisting of tetra-sodium EDTA at concentrations of 20-100 mg/ml (2-10% w/v). The results are shown in FIG. 8.

The results demonstrate that 40 mg/ml (4% w/v) tetra-sodium EDTA is efficacious to kill or to dramatically reduce the population of most organisms after a 24 hour treatment. This concentration of tetra-sodium EDTA is safe for use in connection with humans and other animals and is considered to be efficacious and a desired concentration for antiseptic compositions and methods of the present invention.

Example 4

The Effect of Tetra-Sodium EDTA on *Acanthamoeba* and the Effect of Tetra-Sodium EDTA Treated *Klebsiella* on *Acanthamoeba*

Several species of *Acanthamoeba* are capable of infecting humans and *Acanthamoebic* infections often result as a consequence of improper storage of contact lenses and other medical devices that come into contact with the human body. *Acanthamoebae* feed on bacterial populations and are resistant to many treatments. We tested the effect of tetra-sodium EDTA, prepared as described above on *Acanthamoeba* populations. Tetra-sodium EDTA compositions were also prepared using Pages saline and physiological saline as solvents. We also tested the effect of tetra-sodium EDTA-treated *Klebsiella* on *Acanthamoeba* experimentally using the following methodology.

The Effect of Tetra-Sodium EDTA on *Acanthamoeba*
Method
- Incubate a fresh blood agar plate with *Klebsiella edwardsii* at 37° C. 18 hours prior to testing.
- Using a stock solution of Tetra-sodium EDTA (100 mg/ml.), make a concentration of 22 and 44 mg/mL in Page's saline.
- Place 9 mL of each concentration into a sterile glass test tube. Place 9 mL of sterile Page's saline in to another sterile glass test tube to act as a control.
- Make a suspension of *Klebsiella edwardsii* in 6 mL sterile Page's saline. Adjust to McFarland standard 5.
- Add 1 mL of the suspension to each serial dilution and the control. Due to the dilution factor of the *Klebsiella* suspension each concentration will now be at 20 and 40 mg/mL. The control still contains no Tetra-sodium EDTA. Repeat all the concentrations in physiological saline.
- Vortex to mix. Each tube should now contain a suspension of *Klebsiella* at McFarland 0.5.
- Scrape the surface of the whole of the *Acanthamoeba* plate and suspend in 1.5 mL of Page's saline. Vortex.
- Add 200 uL of the *Acanthamoeba* suspension to each serial dilution and the control.
- Place the test tubes into a 30° C. incubator for 24 hours
- After incubation centrifuge each universal for 10 minutes at 3000 rpm
- Pour off the supernatant and resuspend the pellet
- Place duplicate 10 uL of each dilution and the control onto a non-nutrient agar plate with a lawn of *Klebsiella*. Cut a groove down the center of each plate to prevent migration and place 10 uL of the dilution being tested on each side.
- Mark each inoculation site with a black marker pen.
- Incubate plates for 72 hours at 30° C.
- Check for growth of *Acanthamoeba* by direct visualization of the plates using a ×10 magnification eyepiece light microscope, starting at each inoculation site.

| Growth after 24 hours incubation with tetra-sodium EDTA. | |
|---|---|
| Concentration of EDTA mg/ml. in (solution) | Growth of *Acanthamoeba* |
| 0 (Pages saline) | +++ |
| 0 (Pages saline) | +++ |
| 20 (Pages saline) | ++ |
| 20 (pages saline) | ++ |
| 40 (Pages saline) | − |
| 40 (Pages saline) | − |
| 0 (physiological saline) | +++ |
| 0 (physiological saline) | +++ |
| 20 (physiological saline) | ++ |
| 20 (physiological saline) | ++ |
| 40 (physiological saline) | − |
| 40 (physiological saline) | ++ |

| Growth after 24 hours incubation with tetra-sodium EDTA (repeat) | |
|---|---|
| Concentration of EDTA (mg/mL) | Growth of *Acanthamoeba* |
| 0 (Pages saline) | +++ |
| 0 (Pages saline) | +++ |
| 20 (Pages saline) | ++ |
| 20 (Pages saline) | ++ (trophozoites present) |
| 40 (Pages saline) | − |
| 40 (Pages saline) | − |
| 0 (physiological saline) | +++ |
| 0 (physiological saline) | +++ |
| 20 (physiological saline) | − |
| 20 (physiological saline) | − |
| 40 (physiological saline) | +++ |
| 40 (physiological saline) | ++ (trophozoites present) |

| Growth after 48 hours incubation with tetra-sodium EDTA. | |
|---|---|
| Concentration of EDTA (mg/mL) | Growth of *Acanthamoeba* |
| 0 (Pages saline) | +++ (trophozoites present) |
| 0 (Pages saline) | +++ (trophozoites present) |
| 20 (Pages saline) | − |
| 20 (Pages saline) | − |
| 40 (Pages saline) | − |
| 40 (Pages saline) | − |
| 0 (physiological saline) | +++ |
| 0 (physiological saline) | +++ |
| 20 (physiological saline) | − |
| 20 (physiological saline) | − |
| 40 (physiological saline) | − |
| 40 (physiological saline) | − |

The results demonstrate that 20-40 mg/ml (2-4% w/v) tetra-sodium EDTA in Pages and physiological saline is effective to reduce, or substantially eliminate, *Acanthamoeba* populations after 48 hours of exposure. Tetra-sodium EDTA compositions prepared using water as the solvent were also effective (data not shown). These results indicate that the antiseptic compositions of the present invention are suitable for application as soaking solutions for various medical instruments and devices, including contact lenses and dental/orthodontic/periodontic devices. Antiseptic compositions of the present invention are also effective to substantially eliminate *Acanthamoeba* populations in other applications, including in fresh and sea water storage and distribution systems, in heating, venting and air conditioner units, humidifiers, dialysis units, and the like.

*Acanthamoeba* feed on bacterial populations. We therefore tested whether a bacterial population that was treated with antiseptic EDTA compositions of the present invention would have any effect on *Acanthamoeba* feeding on the treated bacterial population.

The Effect of Tetra-Sodium EDTA Treated *Klebsiella* on *Acaothamoeba*

Method

Incubate a fresh blood agar plate with *Klebsiella edwardsii* at 37° C. 18 hours prior to testing.

Using a stock solution of Tetra-sodium EDTA (100 mg/mL), make a concentration of 22 and 44 mg/mL in Page's saline.

Place 9 mL of each concentration into a sterile glass test tube. Place 9 mL of sterile Page's saline into another sterile glass test tube to act as a control.

Make a suspension of *Klebsiella edwardsii* in 6 mL sterile Page's saline. Adjust to McFarland standard 5.

Add 1 mL of the suspension to each serial dilution and the control. Due to the dilution factor of the *Klebsiella* suspension each concentration will now be at 20 and 40 mg/mL. The control still contains no Tetra-sodium EDTA. Repeat all the concentrations in physiological saline.

Vortex to mix. Each tube should now contain a suspension of *Klebsiella* at McFarland 0.5.

Incubate tubes at 37° C. overnight.

Next day, centrifuge tubes at 300 rpm for 10 minutes. Tip off supernatant; add 10 mL fresh saline or Page's saline, resuspend and re-centrifuge. Tip off supernatant and resuspend in 1 mL of either saline or Page's saline.

Scrape the surface of the whole of the *Acanthamoeba* plate and suspend in 1.5 mL of Page's saline. Vortex.

Add 200 uL of the *Acanthamoeba* suspension to 3 tubes containing 9 mL saline and 3 tubes containing 3 mL Page's saline. Label each tube as if they were the EDTA concentrations used in the incubation with the *Klebsiella*.

Add the 1 mL of resuspended *Klebsiella* to the appropriate tube containing *Acanthamoeba*.

Place the test tubes in to a 30° C. incubator for 24 hours.

Set up another set of tubes to incubate *Klebsiella* with the EDTA at 37° C., overnight as before.

After incubation centrifuge each tube containing the *Acanthamoeba* for 10 minutes at 3000 rpm.

Pour off the supernatant and resuspend the pellet.

Place duplicate 10 uL of each dilution and the control onto a non-nutrient agar plate with a lawn of *Klebsiella* (not incubated with EDTA). Cut a groove down the center of each plate to prevent migration and place 10 uL of the dilution being tested on each side.

Mark each inoculation site with a black marker pen.

Incubate plates at 30° C.

Check for growth of *Acanthamoeba* by direct visualization of the plates using a ×10-magnification eyepiece light microscope, starting at each inoculation site.

Place the remainder of the *Acanthamoeba* suspension into a fresh set of tubes containing either fresh saline or fresh Page's saline.

Wash and resuspend the *Klebsiella*, that has been incubated overnight with the EDTA, as 30 before and add to each appropriate tube containing the *Acanthamoeba*.

Incubate the tubes at 30° C. overnight.

After incubation centrifuge each universal for 10 minutes at 3000 rpm.

Pour off the supernatant and resuspend the pellet.

Place duplicate 10 uL of each dilution and the control onto a non-nutrient agar plate with a lawn of *Klebsiella* (not incubated with EDTA). Cut a groove down the center of each plate to prevent migration and place 10 uL of the dilution being tested on each side.

Mark each inoculation site with a black marker pen.

Incubate plates at 30° C.

Check for growth of *Acanthamoeba* by direct visualization of the plates using a ×10-magnification eyepiece light microscope, starting at each inoculation site.

| Growth of *Acanthamoeba* after 24 hours incubation with *Klebsiella* (previously incubated with EDTA) | |
|---|---|
| Concentration of EDTA (mg/mL) | Growth of *Acanthamoeba* |
| 0 (Pages saline) | +++ |
| 0 (Pages saline) | -- |
| 20 (Pages saline) | ++ |
| 20 (Pages saline) | ++ |
| 40 (Pages saline) | ++ |
| 40 (Pages saline) | - |
| 0 (physiological saline) | +++ |
| 0 (physiological saline) | +++ |
| 20 (physiological saline) | ++ |
| 20 (physiological saline) | ++ |
| 40 (physiological saline) | - |
| 40 (physiological saline) | - |

| Growth of *Acanthamoeba* after 48 hours incubation with *Klebsiella* (previously treated with EDTA) | |
|---|---|
| Concentration of EDTA (mg/ml.) | Growth of *Acanthamoeba* |
| O (Pages saline) | +++ |
| O (Pages saline) | +++ |
| 20 (Pages saline) | + |
| 20 (Pages saline) | - |
| 40 (Pages saline) | - |
| 40 (Pages saline) | - |
| O (physiological saline) | +++ |
| O (physiological saline) | +++ |
| 20 (physiological saline) | - |
| 20 (physiological saline) | - |
| 40 (physiological saline) | - |
| 40 (physiological saline) | - |

These results demonstrate that growth of *Acanthamoeba* can be arrested and *Acanthamoeba* populations can be substantially eliminated by treating bacterial populations on which they feed with antiseptic EDTA compositions of the present invention. Antiseptic EDTA compositions having a tetra-sodium EDTA concentration of from 20-40 mg/ml, (24% w/v) were effective. This substantiates the usefulness of antiseptic compositions of the present invention for applications such as soaking solutions for various medical instruments and devices, including contact lenses and dental/orthodontic/periodontic devices, as well as for other applications such as fresh and sea water storage and distribution systems, in heating, venting and air conditioner units, humidifiers, dialysis units, and the like.

Example 5

Experiments were conducted to determine whether tetrasodium EDTA compositions prevent the attachment of and adherence to silicon tubing of microorganisms. If attachment of and adherence to silicon tubing of microorganisms can be prevented, the formation of biofilms can be reduced. The experimental protocol used and the results obtained are provided below.

Method

Fill 1 cm sections of silicon tubing with molten wax to seal each endolumen, harden at 4° C.

Place 4 sections into 30 mL sterile Phosphate buffered saline (PBS) as a control. Place 8 sections into 30 mL 4% tetra-sodium EDTA.

After 30 minutes, place the 4 sections from the PBS and 4 of the sections from the 4% tetra-sodium EDTA into clean containers on a hot block, and allow to dry.

Transfer the remaining 4 sections into 30 mL sterile PBS to rinse, then allow to air dry as before.

Once dried place all 12 sections into $10^5$ cfu/mL mixed organisms (overnight cultures of *Klebsiella pneumoniae* and CNS grown in nutrient broth at 37° C.), incubate at 37° C.

After 30 minutes remove 2 sections of each type and rinse in 2×30 mL sterile PBS. Air dry as before. Using separate washes and drying vessels for each type prevent contamination.

Place each section into 1 mL PBS in a centrifuge tube, sonicated in a sonicating water bath for 15 minutes.

Plate out each tube, in duplicate, on the automatic plate inoculator, 50 uL on a log dilution.

Incubate the plates at 37° C. overnight. Read colony counts on automatic plate reader Protocol. Repeat after 6 hours.

The results for control and EDTA-treated catheter sections are shown below.

| Type of catheter section | Time of incubation | Number of catheter section | Colony counting NEAT (cfu/mL) | Colony counting 1/10(cfu/mL) |
|---|---|---|---|---|
| Control | 30 min | 1 | 240 | 0 |
|  |  |  | 220 | 0 |
| Control | 30 min | 2 | 280 | 1 |
|  |  |  | 140 | 0 |
| Control | 6 hours | 1 | 1480 | 0 |
|  |  |  | 1120 | 0 |
| Control | 6 hours | 2 | 5200 | 7800 |
|  |  |  | 5467 | 5800 |
| Air-dried EDTA | 30 min | 1 | 240 | 1333 |
|  |  |  | 400 | 800 |
| Air-dried EDTA | 30 min | 2 | 267 | 0 |
|  |  |  | 720 | 0 |
| Air-dried EDTA | 6 hours | 1 | 1280 | 16800 |
|  |  |  | 1120 | 8800 |
| Air-dried EDTA | 6 hours | 2 | 2240 | 21333 |
|  |  |  | 2340 | 16000 |
| Rinsed EDTA | 30 min | 1 | 267 | 0 |
|  |  |  | 379 | 0 |
| Rinsed EDTA | 30 min | 2 | 1040 | 0 |
|  |  |  | 0 | 0 |
| Rinsed EDTA | 6 hours | 1 | 1980 | 9600 |
|  |  |  | 1740 | 12800 |
| Rinsed EDTA | 6 hours | 2 | 3600 | 19000 |
|  |  |  | 3660 | 8600 |

The results for the neat EDTA solution were found to be more reproducible, and these were therefore analysed further. As sections were placed in 1 mL counts per mL are equal to counts per section.

| Type of catheter section | Mean colony count after 30 minutes (cfu/section) | Mean colony count after 6 hours (cfu/section) |
|---|---|---|
| Control | 880 | 3317 |
| Air-dried EDTA | 407 | 1745 |
| Rinsed EDTA | 421 | 2745 |

| Type of catheter section | Mean % reduction in cfu/section from the control after 30 minutes | Mean % reduction in cfu/section from the control after 6 hours |
|---|---|---|
| Air-dried EDTA | 53.8% | 47.4% |
| Rinsed EDTA | 52.2% | 17.3% |

Repeated over 24 hours with *Klebsiella* + CNS:

| Type of catheter section | Mean colony count after 30 minutes (cfu/section) | Mean colony count after 6 hours (cfu/section) | Mean colony count after 24 hours (cfu/section) |
|---|---|---|---|
| Control | 377 | 9205 | 105806 |
| Air-dried EDTA | 273 | 3720 | 70370 |
| Rinsed EDTA | 474 | 9499 | 77051 |

| Type of catheter section | Mean % reduction in cfu/section from the control after 30 minutes | Mean % reduction in cfu/section from the control after 6 hours | Mean % reduction in cfu/section from the control after 24 hours |
|---|---|---|---|
| Air-dried EDTA | 27.4% | 59.6% | 33.5% |
| Rinsed EDTA | +25.7% | +31.9% | 27.2% |

+Denotes increase in mean cfu/section from control

Results for *Pseudomonas aeruginosa*:

| Type of catheter section | Mean colony count after 30 minutes (cfu/section) | Mean colony count after 6 hours (cfu/section) | Mean colony count after 24 hours (cfu/section) |
|---|---|---|---|
| Control | 6400 | 341994 | 1290000 |
| Air-dried EDTA | 4108 | 30000 | 474494 |
| Rinsed EDTA | 5200 | 153758 | 1150000 |

| Type of catheter section | Mean % reduction in cfu/section from the control after 30 minutes | Mean % reduction in cfu/section from the control after 6 hours | Mean % reduction in cfu/section from the control after 24 hours |
|---|---|---|---|
| Air-dried EDTA | 35.8 | 91.2 | 63.2 |
| Rinsed EDTA | 18.8 | 55.0 | 10.9 |

These results demonstrate at least a short term reduction in bacterial populations on both air-dried and rinsed catheter sections.

Example 6

Altered MBC Values when Tetra-Sodium EDTA is Combined with Ethanol

Solutions having a range of tetra-sodium EDTA concentrations (0, 0.1, 0.5, 1, 2, 3, 4 and 8 mg/ml, w/v) were formulated with water and ethanol (to achieve final ethanol concentrations of 0, 0.1, 0.5, 1, 5, 10, 20 and 40%, in water) to test the efficacy of EDTA solutions alone, with alcohol solutions alone, and with EDTA/alcohol solutions. Concentrated stock solutions of tetra-sodium EDTA were prepared in distilled water and ethanol was added to the concentrated aqueous stock solutions to provide the appropriate ethanol concentration.

Method
  Culture an organism in nutrient broth overnight at 37° C.
  Stock solutions of alcohol and tetra-sodium EDTA are used to fill in a grid pattern in 96 well plates (one per culture), using EDTA solutions having 0, 0.1, 0.5, 1, 2, 3, 4 and 8 mg/ml tetra-sodium concentration, w/v, in isopropyl alcohol solvents containing 0, 0.1, 0.5, 1.5, 10, 20 and 40% alcohol, v/v, in water.
  Each well contains 150 uL of each diluent and 50 uL of organism at 1×10⁸ cfu/mL.
  At time periods of 5 minutes, 6 hours and 24 hours each well is cultured by placing a 96 pin lid over the plate (and into each well) then transferring the lid to a 96 well plates, containing 300 uL fresh nutrient broth in each well. Incubate overnight at 37° C. Incubate each inoculum plate at 37° C. during incubation period.
  Record the turbidity of each well after 24 hours.

The results for several organisms are shown below.

| Organism | MBC tetra-sodium EDTA (mg/mL) | MBC alcohol (%) | MBC tetra-sodium EDTA (mg/mL) + alcohol (%) |
|---|---|---|---|
| E. coli | 3 | 10 | 0.5 and 0.5 |
| Proteus sp, | 3 | 10 | 2 and 1 |
| CNS (I) | 8 | 10 | 2 and 1 |
| Klebsiella sp. | 8 | 10 | 1 and 1 |
| Staphylococcus aureus | 0.1 | 0.1 | 0.1 and 0.1 |
| Pseudomonas sp. | 2 | 10 | 2 and 1 |
| CNS (IT) | 8 | 10 | 0.5 and 0.5 |

Tetra-sodium EDTA solutions in water were more effective in killing the microorganisms tested than were the ethanol (alone) solutions. Combination tetra-sodium EDTA in alcohol solutions killed the microorganisms tested at the lowest concentrations. The 2 mg/ml tetra-EDTA in 1% alcohol solution provided excellent results and had a bactericidal effect on all organisms tested. This antiseptic solution is effective at lower concentrations of tetra-sodium EDTA and ethanol than tetra-sodium EDTA solutions in water and than ethanol alone, and it is cost effective, safe and convenient to make and use. In addition to solution formulations, antiseptic compositions of the present invention comprehend EDTA in a mixed aqueous solvent and ethanol for topical use.

Example 7

Solubility of Tetra-Sodium EDTA in Ethanol and Effect on pH

The solubility of tetra-sodium EDTA in ethanol was tested, and the pH of various tetra-sodium solutions in alcohol solvents was measured Method
  Tetra-sodium EDTA was weighed out in duplicates though the range 10-100 mg in 1.5 mL size Eppendorf tubes. 1 mL of 74% Ethanol was added to each tube and vortexed for 30 s.
  To the duplicate set of weighed Tetra-sodium EDTA, 0.5 ml sterile distilled water was added and vortex mixed, followed by 0.5 ml of 74% Ethanol.
  Each of the tubes of Tetra-sodium EDTA was tested for pH where solubility was observed.

The experimental results demonstrated that tetra-sodium EDTA was completely insoluble in a 74% Ethanol solution. The results furthermore demonstrated that, when tetra-sodium was dissolved in distilled water in concentrations in the range of 10-100 mg/ml, w/v, the tetra-sodium EDTA remained in solution when ethanol was added. A preferred technique thus involves solubilizing EDTA salt(s) in an aqueous solution first, and then adding ethanol or another solvent in which the EDTA salt(s) are less soluble, or insoluble. Prepared in this fashion, EDTA salt solutions are expected to be stable over time. The measured pH values for various solutions were as follows:

| 74% Ethanol, alone | pH 7.8 |
| Water | pH 7.1 |
| +10 mg tetra-EDTA | pH 9.0 |
| +20 mg tetra-EDTA | pH 10.8 |
| +40 mg tetra-EDTA | pH 11 |
| +80 mg tetra-EDTA | pH 11.15 |
| +100 mg tetra-EDTA | pH 11.25 |

Example 8

Effect of Autoclaving at 121° C. On Tetra-Sodium EDTA Solutions

We tested the effect of autoclaving on tetra-sodium EDTA solutions to determine whether autoclaving could be used to sterilize tetra-sodium EDTA solutions prior to use. The methodology used and results are described below.

Method
  Make duplicates of 0, 20, 80 and 100 mg/mL of Tetra-sodium EDTA in sterile water and sterile, molten nutrient agar at 50° C.
  Leave one set at room temperature (not heated) and autoclave one set (heated).
  Next day place all agar bottles in a steamer to melt for 40 minutes.

Measuring the Zones of Diffusion
  Using a cork borer, punch out two holes in 16 fresh blood agar plates.
  Make a 0.5 McFarland suspension of CNS and spread using a sterile swab over the plates to create a lawn.
  Pipette 150 uL of each of the Tetra-sodium solutions into duplicate punched out holes and incubate at 37° C. overnight.
  Next day measure the zones of diffusion and record the results.

The results, measured in zone sizes (mm), are presented below. The zone sizes of the controls were plotted against concentration, to allow determination of actual EDTA concentrations in the test samples, which are also presented below. These results demonstrate that autoclaving of tetra-sodium EDTA compositions, whether in sterile water or in agar, does not materially affect the antimicrobial activity of the tetra-sodium EDTA compositions.

| Zone sizes in mm | | | | |
|---|---|---|---|---|
| Concentration of EDTA mg/mL | EDTA in Sterile Water (control) | EDTA in autoclaved Sterile Water | EDTA in Agar | EDTA in autoclaved Agar |
| 0 | 0 | 0 | 0 | 0 |
|   | 0 | 0 | 0 | 0 |
| 20 | 13.2 | 11.6 | 13.5 | 12.7 |
|   | 13.2 | 11.6 | 13.5 | 12.7 |
| 80 | 16.1 | 15.2 | 17.2 | 15.3 |
|   | 16.1 | 15.2 | 17.2 | 15.3 |

-continued

| Zone sizes in mm | | | | |
|---|---|---|---|---|
| Concentration of EDTA mg/mL | EDTA in Sterile Water (control) | EDTA in autoclaved Sterile Water | EDTA in Agar | EDTA in autoclaved Agar |
| 100 | 17.1 | 17.0 | 17.1 | 16.4 |
|  | 17.1 | 17.0 | 17.1 | 16.4 |

| Actual concentration of EDTA | | | | |
|---|---|---|---|---|
| Concentration of initial EDTA mg/mL | EDTA in Sterile Water (control) | EDTA in autoclaved Sterile Water | EDTA in Agar | EDTA in autoclaved Agar |
| 0 | 0 | 0 | 0 | 0 |
| 20 | 20 | 16 | 26 | 19 |
| 80 | 80 | 60 | 101 | 62 |
| 100 | 100 | 98 | 100 | 83 |

Example 9

Effect of Autoclaving at 121° C. On Different Formulations of EDTA

We tested the effect of autoclaving on different formulations of EDTA solutions to determine whether autoclaving could be used to sterilize various EDTA solutions prior to use. The methodology used and results are described below.

Method

Make Up the Agar

Place 50 mL of Nutrient agar solution into 7×100 mL sterile glass bottles.

Add no EDTA powder to the first bottle (labelled 0).

Add 2000 mg of EDTA powder to the second bottle (labelled 40 mg/mL auto).

Add 4000 mg of EDTA powder to the third bottle (labelled 80 mg/mg auto).

Add 5000 mg of EDTA powder to the fourth bottle (labelled 100 mg/mL auto.

Add no EDTA to bottles five, six and seven (but label them 40, 80 and 100 mg/mL NON 25 autoclaved), leave at room temperature.

Do this for each EDTA formulation to test, and autoclave all bottles, marker auto, at 121° C. for 20 minutes.

Next day Place all bottle in a steam bath to melt the agar for pouring.

Once melted allow to cool to 50° C. before adding the appropriate amount of EDTA to the bottles labelled NON autoclaved. All bottles are now ready to be tested.

Measuring the Zones of Diffusion

Using a cork borer, punch out 2 holes in 7 fresh blood agar plates.

Make a 0.5 McFarland suspension of CNS and spread using a sterile swab over the plates to create a lawn.

Pipette 150 ul of each bottle into 2 separate 'punched out holes' and incubate at 37° C. overnight.

Do this for each EDTA formulation.

Next day measure the zones of diffusion and record results. Duplicate holes were used and 2 measurements per zone were made.

Cupric and ferric EDTA solutions did not produce any zones. The effect of heat upon these solutions therefore cannot be measured using this method. The zone sizes measured for di-ammonium EDTA, di-potassium EDTA and magnesium EDTA solutions are provided below. The zone sizes of the controls (no heat) were plotted against concentration to allow determination of actual EDTA concentrations in the test (heated) samples, and results are provided below.

| Zones sizes (mm) | | | | | | |
|---|---|---|---|---|---|---|
| Concentration of EDTA (mg/mL) | Di-ammonium EDTA No heat | Di-ammonium EDTA Heated | Di-potassium EDTA No heat | Di-potassium EDTA Heated | Magnesium EDTA No heat | Magnesium EDTA Heated |
| 0 | 0 | 0 | 0 | 0 | 0 | 0 |
|  | 0 | 0 | 0 | 0 | 0 | 0 |
|  | 0 | 0 | 0 | 0 | 0 | 0 |
|  | 0 | 0 | 0 | 0 | 0 | 0 |
| 40 | 18.3 | 17.9 | 16.2 | 15.5 | 6.8 | 10.6 |
|  | 18.3 | 17.9 | 16.2 | 15.5 | 6.8 | 10.6 |
|  | 18.3 | 17.9 | 16.2 | 15.5 | 6.8 | 10.6 |
|  | 18.3 | 17.9 | 16.2 | 15.5 | 6.8 | 10.6 |
| 80 | 19.7 | 19.7 | 18.9 | 18.3 | 10.0 | 10.8 |
|  | 19.7 | 19.7 | 18.9 | 18.3 | 10.0 | 10.8 |
|  | 19.7 | 19.7 | 18.9 | 18.3 | 10.0 | 10.8 |
|  | 19.7 | 19.7 | 18.9 | 18.3 | 10.0 | 10.8 |
| 100 | 20.0 | 20.6 | 18.2 | 20.0 | 8.3 | 11.8 |
|  | 20.0 | 20.6 | 18.2 | 20.0 | 8.3 | 11.8 |
|  | 20.0 | 20.6 | 18.2 | 20.0 | 8.3 | 11.8 |
|  | 20.0 | 20.6 | 18.2 | 20.0 | 8.3 | 11.8 |

| Actual values of autoclaved EDTA | | | |
|---|---|---|---|
| Concentration of EDTA mg/mL | Di-ammonium EDTA heated | Di-potassium EDTA heated | Magnesium EDTA heated |
| 0 | 0 | 0 | 0 |
| 40 | 39 | 38 | >140 |
| 80 | 80 | 71 | >140 |
| 100 | 150 | >140 | >140 |

The results demonstrate that autoclaving did not diminish the efficacy of most EDTA salt compositions and autoclaving of antiseptic compositions of the present invention may therefore be carried out following preparation to provide sterile antiseptic compositions.

Example 10 pH values of EDTA salts, calcium chloride and Sodium Citrate The pH values of various EDTA salt, calcium chloride and sodium citrate solutions, using distilled water as the solvent, and at specified concentrations, were measured. Results are shown below.

| | |
|---|---|
| Free acid EDTA 10% | pH 4.7 |
| Di-ammonium EDTA 10% | pH 4.38 |
| Calcium Sodium EDTA 10% | pH 6.68 |
| Di-potassium EDTA 10% | pH 4.5 |
| Copper EDTA 10% | pH 6.15 |
| Tetra-sodium EDTA 10% | pH 11.6 |
| 2% | pH 11 |
| Calcium chloride neutralised TS EDTA | pH 7.3 |
| Calcium chloride, 1 molar | pH 3.8 |
| Sodium citrate 50%, 25% | pH 8.5 |

Example 11

Confirmation of the Anti-Coagulant Properties of EDTA Solutions

We verified the anti-coagulant properties of EDTA solutions using the following methodology Method 100 ul aliquots of a range of concentrations (0.5-100 mg/mL) of tetra-sodium or di-sodium EDTA solutions, adjusted to a pH of 11.0-11.6, were placed in plastic capped tubes.

900 uL of fresh blood from healthy volunteers was added to each aliquot of EDTA solution and mixed gently by inversion of the blood tubes at regular intervals.

The results revealed that control tubes containing blood without EDTA solution had clotting times of 10-23 minutes. Tubes containing di-sodium EDTA solutions all had clotting times in excess of 5 days. Tetra-sodium EDTA tubes >1 mg/mL had clotting times in excess of 5 days. Tetra-sodium EDTA tubes having a concentration of 0.5 mg/mL clotted in 28 minutes. Tetra-sodium EDTA is therefore effective as an anticoagulant at concentrations in excess of 1 mg/ml (1% w/v).

Example 12

Osmolarity of Tetra-Sodium Salt Suspensions

The osmolarity and red cell lysis of tetra-sodium EDTA solutions in water and physiological saline having various concentrations was tested using standard laboratory techniques. Red cell lysis was tested by adding 50 ul EDTA blood in 2 ml each concentration 10 of each solution for 2 hours. The Plasma Osmolarity range was 275-295 mlosmol.

| | Osmolarity | Red Cell Lysis |
|---|---|---|
| 2% Tet Sod EDTA in Distilled Water | 142 m/osmol | ++ |
| 4% Tet Sod EDTA in Distilled Water | 277 | + |
| 2% Tet Sod EDTA in Physiological Saline | 219 | +/− |
| 4% Tet Sod EDTA in Physiological Saline | 588 | − |

Example 13

Efficacy of Three EDTA Salts on the Dissolution of Artificial Urine Crystals (AUC)

One problem with urinary catheters is that urine crystals tend to accumulate on the surface of the catheter. The deposit of urine crystals may promote microbial colonization and/or the formation of biofilms, as well as reducing flow through the catheter. It would be desirable to use a sanitizing composition in connection with urinary catheters that reduces the formation of urine crystals. The efficacy of three EDTA salt solutions on the dissolution of artificial urine crystals was tested using the methodology described below.

Materials:
　Artificial urine in 25 ml plastic universal container with urease, incubated at 45° C. for 7 days.
　Di-ammonium, Di-potassium and tetra-sodium EDTA solutions at 100 mg/ml.

Method:
　Centrifuge artificial urine crystals at 4000 rpm for 2 mins.
　Decant supernatant and wash crystals in water followed by centrifugation.
　Resuspend crystals to 1 ml in water and aliquot 200 ul into four universal containers.
　Add 4 ml 100 mg/ml solution of each EDTA salt and water as a control to each universal at room temp.
　After 1, 2 and 3 hours visually observe dissolution of crystals compared to the control.

The results are shown below. All of the EDTA salt solutions reduced the urine crystal deposit compared to an aqueous solution. EDTA salt solutions are therefore suitable for use with urinary catheters.

| Solution | Crystal Deposit |
|---|---|
| Water + AUC | +++++ |
| Tetra-sodium EDTA + AUC | ++ |
| Di-ammonium EDTA + AUC | + |
| Di-potassium EDTA + AUC | +/ |

What is claimed is:

1. A method for disinfecting a catheter, comprising:
introducing a solution into an interior lumen of a catheter, wherein the solution comprises at least one ethylene diamine tetra acidic acid (EDTA) salt and a solvent, wherein the at least one EDTA salt comprises tetra-sodium EDTA and excludes di-sodium EDTA, wherein the solution is at a pH greater than 9.5 and a concentration of greater than 1.5% (w/v) EDTA and less than 6% (w/v) EDTA, wherein the solution has a broad-spectrum bactericidal effect over a wide spectrum of microbes, wherein the solution is biocompatible with human tissue and blood, wherein the solvent comprises ethanol.

2. The method of claim 1, wherein the solvent further comprises water, saline or a combination of both.

3. The method of claim 1, wherein the solution further comprises a proteolytic.

4. The method of claim 1, wherein the introducing comprises filling, locking, flushing or coating the catheter with the disinfectant solution.

5. The method of claim 1, wherein the catheter is a urological catheter or other medical conduit that is inserted into a bladder of a person.

6. The method of claim 1, wherein the catheter is a central venous catheter or medical conduit that is inserted into a bloodstream of a person.

7. The method of claim 1, wherein the at least one EDTA salt further comprises tri-sodium EDTA.

8. A method for disinfecting a catheter, comprising:
introducing a solution into an interior lumen of a catheter,
wherein the solution comprises at least one ethylene diamine tetra acidic acid (EDTA) salt and a solvent,
wherein the at least one EDTA salt comprises tetra-sodium EDTA and excludes di-sodium EDTA,
wherein the solution is at a pH greater than 9.5 and a concentration of greater than 1.5% (w/v) EDTA and less than 6% (w/v) EDTA,
wherein the solution has a broad-spectrum bactericidal effect over a wide spectrum of microbes,
wherein the solution is biocompatible with human tissue and blood, wherein the solvent comprises up to 40% (v/v) ethanol.

9. The method of claim 8, wherein the solvent further comprises water, saline or a combination of both.

10. The method of claim 8, wherein the solution further comprises a proteolytic.

11. The method of claim 8, wherein the introducing comprises filling, locking, flushing or coating the catheter with the disinfectant solution.

12. The method of claim 8, wherein the catheter is a urological catheter or other medical conduit that is inserted into a bladder of a person.

13. The method of claim 8, wherein the catheter is a central venous catheter or medical conduit that is inserted into a bloodstream of a person.

14. The method of claim 8, wherein the at least one EDTA salt further comprises tri-sodium EDTA.

* * * * *